United States Patent [19]

Kawamata et al.

[11] Patent Number: 4,751,217

[45] Date of Patent: Jun. 14, 1988

[54] PHYSIOLOGICALLY ACTIVE SUBSTANCES NAMED SEN-366

[75] Inventors: Masanobu Kawamata, Kyoto; Yoji Ezure; Nobutoshi Ojima, both of Shiga; Kiyotaka Konno, Kyoto; Teruya Nakamura; Hideyuki Yasuda, both of Shiga, all of Japan

[73] Assignees: Nippon Shinyaku Co., Ltd.; Takara Shuzo Co., Ltd., both of Japan

[21] Appl. No.: 790,266

[22] Filed: Oct. 22, 1985

[30] Foreign Application Priority Data

Oct. 22, 1984 [JP] Japan .................................. 59-222740
Jul. 12, 1985 [JP] Japan .................................. 60-154925
Aug. 27, 1985 [JP] Japan .................................. 60-189193
Aug. 30, 1985 [JP] Japan .................................. 60-192756

[51] Int. Cl.$^4$ .................. A61K 31/70; C07H 3/06; C07H 15/04
[52] U.S. Cl. ........................................ 514/25; 514/23; 514/33; 514/54; 536/1.1; 536/4.1; 536/123
[58] Field of Search ............... 536/4.1, 1.1, 123, 4.1; 514/23, 25, 53, 54

[56] References Cited

U.S. PATENT DOCUMENTS 4,521,592 6/1985 Dahmen et al. ................. 536/4.1

OTHER PUBLICATIONS

March, *Advanced Organic Chemistry; Reactions, Mechanisms, and Structure*, 1968, pp. 581 and 753.
Cram et al. *Organic Chemistry* 2nd Ed., 1964, pp. 176 and 589–590.
Hilgetag et al, *Preparative Organic Chemistry*, published by John Wiley & Sons, 1972, p. 816.
*The Merck Index*, published by Merck & Co., Inc., 1976, p. 1033, no. 7752.

Primary Examiner—J. R. Brown
Assistant Examiner—Elli Peselev
Attorney, Agent, or Firm—Jacobs & Jacobs

[57] ABSTRACT

A compound of the formula (I):

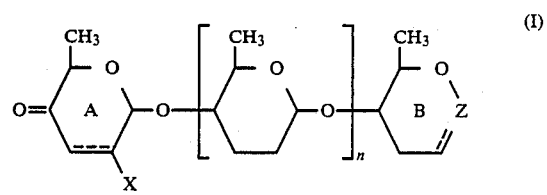

in which: -----
is a single bond or a double bond,
X is hydrogen or hydroxy,
n is 0 or 1,
Z is

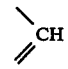

when ----- in ring B is a double bond, and, when ----- in ring B is a single bond, Z is

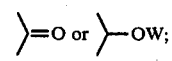

wherein W is hydrogen, lower acyl, unsubstituted arylcarbonyl, lower alkyl or substituted arylcarbonyl.

These compounds are useful as platelet aggregation inhibitors.

8 Claims, 28 Drawing Sheets

PHYSIOLOGICALLY ACTIVE SUBSTANCES NAMED SEN-366

The present invention relates to physiologically active substances named SEN-366 that are useful as pharmaceuticals and their manufacture and, more particularly, it relates to physiologically active substances named SEN-366 that have the following general formula (I) and their manufacture:

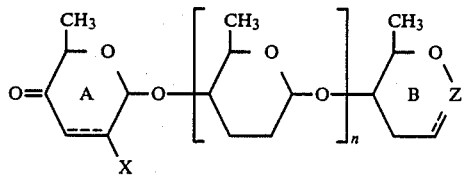

in which:
≡≡ is a single bond or a double bond,
X is hydrogen or hydroxy,
n is 0 or 1, and
Z is

when ≡≡ in ring B is a double bond and, when ≡≡ in ring B is a single bond, Z is

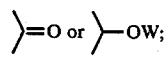

wherein W is hydrogen, lower acyl, unsubstituted arylcarbonyl, lower alkyl or substituted arylcarbonyl.

Useful compounds of the invention include compounds of formulas (II), (V), (VIII) and (X).

Compounds of formula II are of the formula

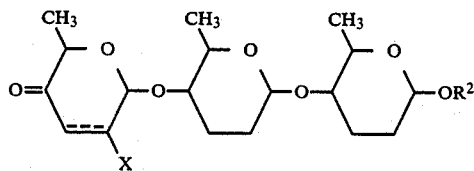

in which $R^2$ is hydrogen, lower acyl or unsubstituted arylcarbonyl; X is hydrogen or hydroxy; and ≡≡ is a single or double bond.

Compounds of formula V are of the formula:

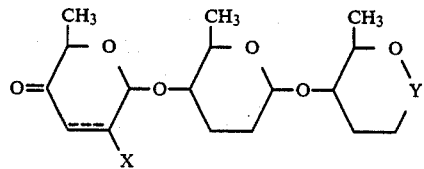

in which Y is =C=O or =CHOR$^5$ where R$^5$ is $C_{1-4}$ lower alkyl or substituted arylcarbonyl; X is hydrogen or hydroxy; and ≡≡ is a single or double bond.

Compounds of formula VIII are of the formula:

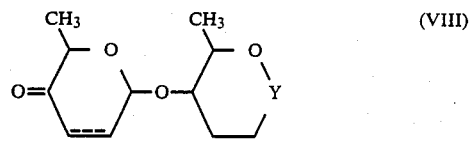

in which Y is =C=O or =CHOR$^8$ where R$^8$ is hydrogen, lower alkyl, lower acyl or substituted or unsubstituted arylcarbonyl and ≡≡ is a single or double bond.

Compounds of formula X are of the formula:

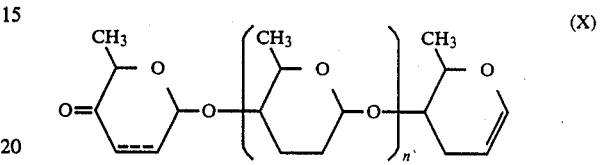

in which n is 0 or 1; and ≡≡ is a single or double bond.

In the above formulas, lower alkyl may be either straight or branched chain alkyl of 1 to 4 carbon atoms and the aryl moiety in the substituted or unsubstituted arylcarbonyl is preferably phenyl. Illustrative of substituted arylcarbonyl is phenylcarbonyl substituted in the phenyl moiety by 1 to 5 halogen, preferably chlorine or fluorine. Lower acyl may be carboxylic acyl of 2 to 6 carbon atoms, and is preferably straight or branched chain alkanoyl of 2 to 6 carbon atoms.

As will be described in more detail hereinafter, compounds 366-D (Formula II, $R^2$ and X are hydrogen and ≡≡ is a single or double bond), 366-P (Formula II, $R^2$ is hydrogen, X is hydroxy and ≡≡ is a single bond) and 366-F (Formula VIII, Y is =CHOR$^8$, where R$^8$ is hydrogen, and ≡≡ is a single or double bond) are obtained directly from culturing a microorganism.

SEN-366-P may be represented by the formula III:

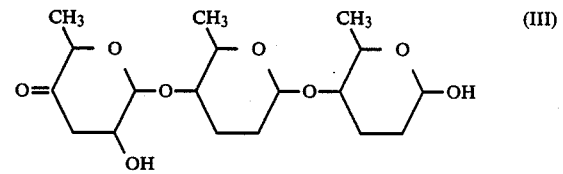

In recent years, blood vessel diseases have increased in frequency of occurrence and difficulty of therapy. Blood vessel diseases are numerous and include acute myocardial infarction, thrombus obstructive angitis, obstructive arteriosclerosis, chronic glomerulonephrisis, nephrose syndrome, cerebral arteriosclerosis, cerebral thrombosis sequela, angita pectoris, diseases observed in patients after intracardiac operations, chronic renal insufficiency of patients who are receiving dialysis for more than one month; local anemia, thrombosis observed in patients equipped with auxiliary apparatuses such as artificial heart or artificial kidney, and the like. Platelet aggregation inhibitors have been used for the prevention and treatment of thrombosis. For example, ticlopidine is administered to patients with thrombus obstructive angitis and chronic kidney insufficiency during dialysis and to those who have had a cardiac operation.

It is also known that platelet aggregation inhibitors can be useful as substances inhibiting metastasis of cancer.

Several kinds of platelet aggregation inhibitors derived from microorganisms are known and their usefulness as pharmaceuticals has been studied. For instance, WF-5239 from Aspergillus genus (cf. Journal of Antibiotics, vol. 37, No. 5, pages 469–474) and SEN-128-B (cf. Japanese Patent Application Unexamined 59/095893) are known.

The present invention provides improved platelet aggregation inhibitors in terms of both effect and safety, which are entirely different from the known platelet aggregation inhibitors in chemical structure.

The compounds of the present invention markedly inhibit the aggregation of platelets. They are obtained from the metabolic products of a microorganism freshly isolated from soil or obtained by a chemical modification of such produced substances.

The microorganism used in the present invention as more fully illustrated later, belongs to the Streptomyces genus and, as stated above, SEN-366-D, SEN-366-P and SEN-366-F are each directly produced by the microorganism.

SEN-366-D is formed as a mixture of four compounds with similar properties that can be separated by forming acetyl derivatives thereof (named SEN-366-A). It has been confirmed that those four substances are new physiologically active substances that differ as to their steric configurations (alpha and beta anomers) of $OR^2$ [$R^2$ is acetyl in formula (II) in the 2-pyranol ring] and the degree of unsaturation in the pyran-3-one ring. Acetyl derivatives of these four substances are named SEN-A$_1$, A$_2$, A$_3$ and A$_4$. Their differentiation in structures is as given below, with respect to formula II.

|  | X | Configuration of $OR^2$ | === |
| --- | --- | --- | --- |
| SEN-366-A$_1$ | H | alpha | double bond |
| A$_2$ | H | alpha | single bond |
| A$_3$ | H | beta | double bond |
| A$_4$ | H | beta | single bond |

As hereinafter, the subscripts 1, 2, 3 and 4 are given to the compounds corresponding to A$_1$ to A$_4$, respectively, in terms of $OR^2$ configuration and the degree of unsaturation ===.

Starting from SEN-366-D which is compound (II) where $R^2$ and X are hydrogen and === is a single or double bond, lower acyl derivatives and arylcarbonyl derivatives can be synthesized and isolated. For example, the following benzoyl compounds (SEN-366-B) where $R^2$ is benzoyl, X is hydrogen, and === is a single or double bond in the formula (II) in which the degree of unsaturation in the pyran-3-one ring and the steric configuration of $OR^2$ are different (alpha and beta anomers) can be obtained.

|  | Configuration of OR | === |
| --- | --- | --- |
| SEN-366-B$_1$ | alpha | double bond |
| B$_2$ | alpha | single bond |
| B$_3$ | beta | double bond |
| B$_4$ | beta | single bond |

SEN-366-D and derivatives thereof have low toxicity and strong platelet aggregation inhibiting action. Thus, as more fully illustrated later referring to biological properties, SEN-366-D and derivatives thereof markedly inhibit the platelet aggregation action in rabbits wherein adenosine-5'-diphosphate (ADP), arachidoic acid (AA) or collagen are used as platelet aggregation inducers. Accordingly, the compounds of the present invention are useful as pharmaceuticals in the prevention and therapy of the aforementioned thrombosis.

Representative strains producing compounds SEN-366-D, SEN-366-F and SEN-366-P according to the present invention were obtained by the present inventors from the soil in the Prefecture of Kyoto. Their mycological properties are as follows. Incidentally the experiment for the identification was conducted in accordance with the method disclosed in the International Streptomyces Project (ISP). The media used were those described in ISP or in Examining Standard "Applied Microbiology Industry" by the Japanese Patent Office and, as to those which are not described in the above, the media exemplified in S. A. Waksman: The Actinomyces, vol. 2, 1961 were used. Description of the color tone is in accordance with "Color Harmony Manual" by Container Corporation of America.

(1) Description according to a method by ISP.

(a) Morphological Characteristics.

Under a microscope, many aerial mycelia were developed from substrate mycelium and their terminals form spirals with 5 to 6 twists. Sometimes, curling form was observed and that is especially frequent in glucose-asparagine-agar medium. Cutting of mycelium and formation of whirls and sporangia are not observed. In accordance with the standard by ISP, this belongs to section spiral. In well-grown spore chains, there are 10 or more spores in series.

When observed by a scanning electron microscope, spores are generally in columns and their sizes are $0.7$–$0.9 \times 1.0$–$1.4 \mu$. Their surfaces are flat and smooth.

The above morphological characteristics are observed in yeast-malt-agar medium, glycerol-asparagine-agar medium, oat meal-agar medium, starch-inorganic salt-agar medium, and other media in which aerial mycelia are well formed.

(b) Color of colonies.

Color tone of aerial mycelia with sufficient spores are gray type color (Tresner Backus Color Wheels) in yeast-malt-agar medium, glycerol-asparagine-agar medium, starch-inorganic salt-agar medium, and oatmeal-agar medium. Representative color tone is gray (3fe to 5fe).

(c) Color of substrate mycelia (reverse side of colony)

Yellow in oatmeal-agar medium. In glycerol-asparagine-agar medium and in yeast-malt-agar medium, it is yellow in early stage but, later, turns brown. In starch-inorganic salt-agar medium, it is pale yellow and gradually turns grayish yellow. Those yellow pigments are pH indicators and turn violet when 0.05N sodium hydroxide is added thereto.

(d) Color of media (soluble pigments).

Production of melanoid is positive in peptone-yeast-iron-agar medium, tyrosine-agar medium and tryptone-yeast broth. Production of other pigment is that, in oatmeal-agar medium, the color is yellow and, in glycerol-asparagine-agar medium and in yeast-malt-agar medium, it is initially yellow and, later, turns yellowish brown. Those yellow type pigments are pH indicators and turn reddish violet to violet when 0.05N sodium hydroxide is added thereto. No production of pigment is observed in starch-inorganic salt-agar medium.

(e) Utilization of carbon sources.

Utilization of sugars listed in ISP: D-Glucose, L-arabinose, D-xylose, D-fructose, rhamnose and D-mannitol are well utilized while sucrose and raffinose are weakly and i-inositol is not utilized.

Utilization of other sugars: Galactose, mannose, maltose, and glycerol are well utilized while lactose and salicine are weakly and inulin is not utilized.

(2) Other Properties.

(a) Properties on culture media (cultured at 27° C. for 14 days).

| Medium | Growth | Mycelia Formation | Color | Color of Mycelia | Soluble Pigment |
|---|---|---|---|---|---|
| Sucrose-Nitrate-Agar | Poor | None | — | Colorless | None |
| Glycerol-Nitrate-Agar | Moderate | Moderate | Gray (3fe) | Brown | Brown |
| Glycerol-Asparagine-Agar | Good | Moderate | Gray (3fe) | Yellowish brown | Yellowish brown |
| Glucose-Asparagine-Agar | Moderate | Moderate | Gray (d-3fe) | Yellow | Yellow |
| Starch-Inorganic salt-Agar | Good | Abundant | Gray (2-3fe) | Gray | None |
| Tyrosine-Agar | Good | Abundant | Gray (3-5fe) | Reddish brown | Reddish brown |
| Nutritive Agar | Moderate | None | — | Pale brown | Pale brown |
| Oatmeal-Agar | Good | Moderate | Gray (d-g) | Yellow | Yellow |
| Yeast-Malt-Agar | Good | Moderate | Gray (3-5fe) | Brown | Yellowish brown |
| Peptone-Yeast-Iron-Agar | Moderate | None | — | Dark brown | Dark brown |
| Emerson's Agar | Good | None | — | Brown | Brown |
| Potato slices | Good | None | — | Dark brown | Dark brown |
| Defatted Milk | Good | None | — | Pale brown | Brown |
| Glucose-Peptone-Gelatin | Good | None | — | Pale brown | Dark brown |
| Triprose-Yeast Broth (cultured for 2 days) | Good | None | — | Pale brown | Dark brown |

(b) Physiological Properties.
1. Liquefaction of gelatin: positive
2. Reduction of nitrates: positive (weakly)
3. Hydrolysis of starch: positive
4. Coagulation of milk: negative
5. Peptonization of milk: positive
6. Formation of hydrogen sulfide: negative
7. Production of melanoid pigments: positive
8. Tyrosinase: positive
9. Decomposition of cellulose: negative
10. Temperature range for growth: 10–30° C. (optimum temperature being 25–27° C.)
11. pH Range for growth: 4.0–9.2 (optimum pH being 6.0–7.6)

Mycological properties of the SEN-366 strain will be summarized to be as follows. Thus, it produces aerial mycelia of gray type color; chain formed by spores is in spiral and the spore surface is smooth; subtrate mycelia are yellow to brown, soluble pigments are yellow to yellowish brown and those pigments are pH indicators which turn violet when 0.05N sodium hydroxide is added thereto; melanine is positive.

Taking the above given mycological properties into consideration, the present inventors have identified that the microorganism relating to the present invention belongs to a category of Streptomyces galilaeus. Since the microorganism used in the present invention has a characteristic feature of producing SEN-366-D and/or SEN-366-P and/or SEN-366-F, it has been named Streptomyces sp. SEN-366. This strain was deposited at the Fermentation Research Institute, Agency of Industrial Science and Technology, Japan, on June 28, 1984 and received deposit number FERM BP-557.

In the present invention, all sorts of strains belongong to Streptomyces in addition to the above-given strain can be used so far as they produce SEN-366-D and/or SEN-366-P and/or SEN-366-F. Further, there are several SEN-366-D and/or SEN-366-P productive strains which are artificial mutants (obtained by treating with ultra-violet ray or with mutant-inducers for microorganisms such as nitrosoguanidine) or which are natural mutants and, needless to say, such mutants can be used in the present invention too.

In carrying out the present invention, microorganism which produce SEN-366-D and/or SEN-366-P and/or SEN-366-F is cultured by conventional way. Thus, the medium may be either liquid or solid and, generally, shake culture or culture by stirring with air using a liquid medium is applied. Any medium may be used so far as it is suitable for growth of Actinomycetes and it produces SEN-366-D and/or SEN-366-P and/or SEN-366-F.

Suitable carbon sources are glucose, sucrose, maltose, glycerol, dextrin, starch powder and the like and suitable nitrogen sources are soybean powder, peptone, yeast extract, meat extract, corn steep liquor, ammonium chloride, and the like. Addition of suitable amounts of sodium chloride, potassium chloride, potassium carbonate, various phosphates, etc. may cause good result. Suitable amounts of iron, magnesium, etc. may be added too. If necessary, vitamins or antifoaming agent (in order to inhibit formation of foams during fermentation) may also be added.

Culturing conditions such as the pH of the medium, culturing temperature, etc. may be changed adequately within a range or limitation that SEN-366-D and/or SEN-366-P are/is produced therein. For instance, pH is preferably 6–8 and temperature is preferably 22°–30° C. (more preferably 24°–27° C.) in case of a shake culture or aeration/stirring culture. The time for the culturing may depend upon the scale and other circumstances and, usually, it is for 1 to 7 days whereupon SEN-366-D and SEN-366-P are produced in the culture liquid.

Substances of the present invention are present in both culture filtrate and bacterial body and may be obtained from any of them. In isolating SEN-366-D and/ir SEN-366-P and/or SEN-366-F from the filtrate or from bacterial body, widely accepted conventional means can be used.

For example, filtration, centrifugation, extraction with various organic solvents (such as acetates, alcohols, ketones, ethers, etc.), adsorption/elution using various adsorbents (such as silica gel, alumina, etc.), chromatography, gel filtration, partition chromatography, etc. can be solely or jointly applied.

More specifically, the culture filtrate or mycelium is extracted with organic solvent such as ethyl acetate or with acetone, then the culture filtrate, the above extract or a solution containing the present invention substances is passed through a column in which adsorbent such as silica gel (e.g. Wakogel C-300), and adsorbed substances are eluted with methanol, chloroform, ethyl acetate, n-hexane, and/or other organic solvents. If necessary, the eluate is treated with activated charcoal such as Darco G-60, made adsorbed in a column in which adsorbent such as silica gel is filled, eluted with n-hexane, ethyl acetate and/or other organic solvent, and the solvent is evaporated from the eluate to give oily SEN-366-D and/or SEN-366-P.

SEN-366-P, which is of formula (III), is then heated at 30°–120° C. for 10 minutes to 18 hours (more preferably, at 90°–100° C. for 15–60 minutes) to give an olefinic compound (IV), which is one of the SEN-366-D compounds.

(IV)

Alternatively, when a solution or culture filtrate containing the SEN-366-P is heated the same as above and then subjected to extraction and purification as already described, it provides an olefinic compound of the SEN-366-D effectively.

When the SEN-366-D thus obtained is conventionally acetylated, purified with silica gel chromatography, and recrystallized, four acetyl derivatives (SEN-366-$A_1$, SEN-366-$A_2$, SEN-366-$A_3$ and SEN-366-$A_4$) are obtained. Similarly, SEN-366-D is conventionally benzoylated and treated as above to give four kinds of benzoyl derivatives—SEN-366-$B_1$, SEN-366-$B_2$, SEN-366-$B_3$ and SEN-366-$B_4$.

SEN-366-D may be similarly treated to afford lower acyl and arylcarbonyl derivatives.

When the resulting lower acyl or arylcarbonyl derivatives are hydrolyzed by conventional methods, the following substances, for example, are obtained. Thus, olefinic compound (a mixture of the below-given $D_1$ and $D_3$) of SEN-366-D from SEN-366-$A_1$ or SEN-366-$A_3$; and reduced compound (a mixture of below-given $D_2$ and $D_4$) from SEN-366-$A_2$ or SEN-366-$A_4$. When SEN-366-D is subjected to catalytic reduction only the reduced compound (i.e. a mixture of $D_2$ and $D_4$) is obtained.

|  | Configuration of $OR^2$ |  |
| --- | --- | --- |
| SEN-366-$D_1$ | alpha | double bond |
| SEN-366-$D_2$ | alpha | single bond |
| SEN-366-$D_3$ | beta | double bond |
| SEN-366-$D_4$ | beta | single bond |

Properties of the compounds of the present invention are as follows:

| (1) SEN-366-A | | | |
| --- | --- | --- | --- |
|  | Melting Pt | $R_f$ | Sp. Optical Rotation $[\alpha]_D^{25}$ in $CHCl_3$ |
| SEN-366-$A_1$ | 125–127° C. | 0.77 | −75.42 (c = 1.005) |
| SEN-366-$A_2$ | 125–128 | 0.75 | −193.38 (c = 0.544) |
| SEN-366-$A_3$ | oily | 0.75 | −58.35 (c = 0.425) |
| SEN-366-$A_4$ | 129–131 | 0.73 | −163.35 (c = 0.584) |

The $R_f$ values are by a thin layer chromatography using silica gel (Merck Art 5554) and a 2:1 mixture of ethyl acetate/n-hexane.

Infrared spectra: FIG. 1 to FIG. 4

$^1$H-Nuclear magnetic resonance spectra: FIG. 11 to FIG. 14

$^{13}$C-Nuclear magnetic resonance spectra: FIG. 19 to FIG. 22

(2) SEN-366-D: Olefinic type ($D_1$, $D_3$) and reduced type ($D_2$, $D_4$)

Elementary analysis of olefinic type calculated for $C_{18}H_{28}O_7$: C 60.66, H 7.92; Found: C 60.45, H 8.17

Elementary analysis of reduced type calculated for $C_{18}H_{30}O_7$: C 60.31, H 8.44; Found: C 60.29, H 8.52.

Molecular weight: 356 for olefinic and 358 for reduced type.

Solubility: Soluble in methanol, ethanol, chloroform, acetone and ethyl acetate; hardly soluble in water, petroleum ether and n-hexane.

Classification whether acidic, neutral or basic: Neutral.

Color of the substance: colorless oily substance or amorphous powder.

Color reaction: Positive to sulfuric acid and potassium permanganate (pseudo-positive for reduced type); negative to Dragendorf reagent, ninhydrin reagent, and Ehrlich reagent.

Thin-layer chromatography: Silica gel (Merck Art 5554). $R_f$ value is 0.65 for chloroform-methanol (10:1) and 0.32 for ethyl acetate-n-hexane (2:1).

$^1$H nmr spectra: Olefinic type in FIG. 16 and reduced type in FIG. 17 ir spectra: Olefinic type in FIG. 6 and reduced type in FIG. 7

(3) Sen-366-P

Elementary analysis calculated for $C_{18}H_{30}O_8$: C 57.74, H 8.08; Found: C 57.41, H 7.79.

Molecular weight: 374.

Solubility: Soluble in water, methanol, ethanol, chloroform, acetone and ethyl acetate; hardly soluble in petroleum ether and n-hexane.

Classification whether acidic, neutral or basic: Neutral

Color of the substance: Colorless.

Color reaction: positive to sulfuric acid and potassium permanganate and negative to Dragendorf reagent, ninhydrin reagent and Ehrlich reagent.

Thin-layer chromarography: Silica gel (Merck Art 5554). Rf for chloroform/methanol (10:1) is 0.38 anf for ethyl acetate/n-hexane (2:1) is 0.14.

$^1$H nmr spectra: FIG. 18 ir spectra: FIG. 8

(Biological Properties)

Biological properties of the present invention compounds are as follows:

Inhibitory Action against Platelet Aggregation:

(1) Materials and Method:

The sample is tested after dissolved in dimethyl sulfoxide. The preparation is conducted so as to make the final concentration of the solvent 1%. Dimethyl sulfoxide of the same concentration is used as a control. As to inducers for platelet aggregation, ADP (final concentration: 5 μm), AA (arachidonic acid) (final concentration: 150 μM) and collagen (final concentration: 10 μg/ml) are used.

(2) Preparation of platelet:

Blood is taken from total neck artery of male rabbits of 2.0–2.5 kg body weight. To the blood is added 1/10 volume of 3.8% sodium citrate solution, the mixture is gently stirred, centrifuged 1300×g for 2 minutes, and the resulting supernatant liquid is used as plasma with abundant platelet (hereinafter abbreviated as PRP). The precipitate is further centrifuged at 1600×g for 10 minutes and the resulting supernatant liquid is used as plasma with poor platelet (hereinafter abbreviated as PPP).

(3) Method for Measuring Aggregation Power:

A measuring apparatus for platelet aggregation is used and the changes in absorbancy by the aggregation with an elapse of time are recorded.

Thus, 200 microliters of PRP is taken, its difference between PPP is adjusted to a certain value, then 25 microliters of control solution or test solution is added, the mixture is stirred (1000 rpm) for 1 minutes, 25 microliters of aggregation inducer is added, and the changes in absorbancy are recorded. The inhibitory ratio is calculated from the following expression from the maximum aggregation ratio of the control (A in %) and that of the test solution (B in %):

$$\text{Inhibitory Ratio (\%)} = \left(1 - \frac{B}{A}\right) \times 100$$

Inhibitory ratios with varied test solution concentrations are calculated and the IC$_{50}$ (50% inhibitory concentration) is calculated therefrom. The result with the representative compounds of the present invention is given in Table 1.

In the table, SEN-366-BT$_1$ to SEN-366-BT$_4$ are the compounds where R is butyryl.

(Toxicity)

It has been confirmed that the present invention compounds exhibit very low toxicity. For instance, LD$_{50}$ of SEN-366-D to mice is not less than 500 mg/kg and not less than 100 mg/kg by oral administration and by intraperitoneal injection, respectively.

TABLE 1

| SEN-366 | IC$_{50}$ (μg/ml) | | |
|---|---|---|---|
| | Collagen 10 μg/ml | ADP 5 μM | AA 150 μM |
| D | 0.016 | 0.22 | 1.9 |
| A$_1$ | <0.1 | 0.22 | 1.2 |
| A$_2$ | 0.54 | 1.6 | 6.0 |

TABLE 1-continued

| SEN-366 | IC$_{50}$ (μg/ml) | | |
|---|---|---|---|
| | Collagen 10 μg/ml | ADP 5 μM | AA 150 μM |
| A$_3$ | 0.47 | 0.44 | 1.6 |
| A$_4$ | 0.27 | >10 | 5.4 |
| P | 1.6 | 4.4 | 25 |
| B$_1$ | 0.16 | 1.1 | 0.32 |
| B$_2$ | 1.7 | 5.7 | 1.6 |
| B$_3$ | 0.17 | 1.0 | 0.55 |
| B$_4$ | 2.9 | 6.5 | 1.2 |
| BT$_1$ | 0.17 | 1.1 | 1.55 |
| BT$_2$ | 0.53 | 1.35 | 2.1 |
| BT$_3$ | 0.16 | 0.47 | 0.64 |
| BT$_4$ | 1.6 | 5.3 | 5.7 |

As described hereinabove, the present invention compounds exhibit very important biological properties—i.e. inhibitory action against platelet aggregation——and are useful as a remedy for thrombosis, inhibitor for metastasis of cancer, and so forth.

When the present invention compound is used in the treatment or prevention of thromboses in animals, including humans, a platelet aggregation inhibiting effective amount of the compound itself, or a pharmaceutical composition comprising 0.1 t 99.5% of the compound (preferably 0.5 to 90%) in combination with a pharmaceutically acceptable carrier or diluent, is administered to an animal, including humans, in need thereof.

As carriers, one or more of diluent, vehicle or other auxiliary agent in solid, semi-solid or liquid form may be used. It is desired that the pharmaceutical composition is administered in unit dose form. Pharmaceutical compositions of the present invention can be administered by oral, parenteral, topical or rectal routes. Needless to say, pharmaceutical preparations suitable for each route are to be applied. For example, enteric coated tablets or capsules are particularly recommended in oral administration.

It is desired that the dose as platelet aggregation inhibitor is regulated after considering the age, body weight, etc. of the patient, administration route, and kind and degree of the disease. Usually, the dosage is generally 0.1 to 1000 mg for adult per day. In some instances, it is sufficient to use less dose than above while, in some other instances, it will be necessary more dose. When large dose is administered, it is desired to give it separately, i.e. by dividing into some times a day.

Oral administration can be carried out by the use of pharmaceutical preparation forms in solid or liquid unit dosage forms such as, for example, powder, diluted powder, tablet, sugar coated tablet, capsule, granule, suspension, liquid, syrup, drop, sublingual tablet, etc.

Powder can be prepared by pulverizing the active substance in suitable particle size. Diluted powder can be prepared by pulverizing the active substance in suitable particle size followed by mixing with similarly finely powdered pharmaceutical carrier such as, for example, edibel carbohydrate (e.g. starch, mannitol, etc.). If necessary, flavoring agent, preserving agent, dispersing agent, coloring agent, perfume and others may be added thereto.

Capsule can be prepared by filling powder or diluted powder as prepared above or granule prepared by a way as described in the item of tablet into capsule sheath such as gelatin capsule. It is also possible that lubricant or fluidizing agent (such as colloidal silica, talc, magnesium stearate, calcium stearate, solid polyethyleneglycol, and the like) is mixed with the powder followed by filling into capsule sheath. When disintegrating agent or solubilizing agent (such as, for example, carboxymethyl cellulose, carboxymethylcellulose calcium, lowly substituted hydroxypropyl cellulose, calcium carbonate, sodium carbonate, and the like) is added, it is possible to improve the effectiveness of the pharmaceutical when the capsule is administered.

It is also possible that the fine powder of the present invention is suspended or dispersed in vegetable oil, polyethyleneglycol, glycerol, surfactant, etc and then packed with gelatin sheet to give soft capsule preparation. Tablet can be prepared first by preparing powdery mixture, subjecting to making into granule or slug, and adding lubricant or disintegrating agent thereto followed by compressing to make tablets.

Powdery mixture is prepared by mixing the suitably pulverized substance with the above-given diluent or base. If desired, combining agent (such as carboxymethylcellulose sodium, alginate, gelatin, polyvinylpyrrolidone, polyvinyl alcohol, and the like), solubilization retarding agent (such as paraffin), reabsorbing agent (such as quaternary salt) and/or adsorbent (such as bentonite, kaolin, dicalcium phosphate, and the like) may be jointly used. The resulting powdery mixture is then made moistened with a combining agent (such as syrup, starch paste, gum arabicum, cellulose solution or polymer solution) and then passed through a sieve compulsorily to give granules. Instead of preparing granules from powder as such, it is also possible that the starting material is first subjected to a tableting machine and the resulting slug of incomplete shape is pulverized to give granules.

The resulting granules are mixed with lubricant such as stearic acid, stearate, talc, mineral oil, etc. so that their adhesion each other can be prevented. The mixture after addition of lubricant as such is then made into tablets by compression. Instead of making into granules or slug, the pharmaceutical can be mixed with fluidized and inert carrier followed by making into tablets directly. Transparent or semitransparent protective coating (such as closed coating of shellac), coating of sugar or polymer, and brushing-up coating such as wax can be also used.

Other oral administration forms such as solution, syrup, elixier, etc. can be made into unit dose form in which certain quantity of the pharmaceutical is contained in certain amount of the form. Syrup can be manufactured by dissolving the compound into a suitable aqueous solution which is previously given with perfume or flavouring. Elixier is manufactured by the use of nontoxic alcoholic carrier. Suspension is prescribed by dispersing the compound into nontoxic carrier. In those cases, solubilizing agent and emulsifiers (such as ethoxylated isostearyl alcohols, polyoxyethylenesorbitol esters, etc.), preservatives, flavouring agent (such as peppermint oil, saccharine, etc.) and others may also be added if necessary.

If desired, the unit dose form for oral administration is made into microcapsule. Said prescription may be coated or embedded in polymers or wax so that elongation of the acting time or sunstained release can be resulted.

Parenteral administration can be conducted by the use of liquidal unit dose form (such as solution or suspension) for subcutaneous, intramuscular or intravenous injection. Those are manufactured by suspending or dissolving certain amount of the compound into nontoxic liquid carrier suitable for injection such as aqueous or oily solvent followed by sterilizing said suspension or solution. Alternatively, certain amount of the compound is taken into a vial and the vial together with its content is sterized and sealed closely. In order to dissolve or mix immediately before administration, powdered or lyophilized active ingredient is prepared together with vials and carriers. In order to make the injection solution isotonic, nontoxic salt or salt solution may be added thereto. Joint use of stabilizers, preservatives, emulsifiers, etc. is also possible.

Rectal administration is conducted by the use of suppositories prepared by mixing the compound with low-melting and water-soluble or insoluble solid (such as polyethyleneglycol, cacao butter, higher esters such as myristyl palmitate, etc.) or a mixture thereof.

To the preparations of the present invention, it is possible to add other pharmaceuticals such as ticlopidine to the active ingredient of the present invention. Alternatively, such other pharmaceuticals may be jointly administered.

(EXAMPLES)

The present invention is further illustrated by way of the following examples which are not limitative, of course.

EXAMPLE 1

Manufacture of SEN-366-D, $A_{1-4}$, $B_{1-4}$, $D_1$, $D_3$, and $D_2$ and $D_4$.

(1) A slant culture of Streptomyces sp. SEN-366 was inoculated to a 500 ml Erlenmeyer flask containing 100 ml sterilized seed medium (containing 2% of soluble starch, 1% of soybean flour powder, 0.5% of sodium chloride, 0.05% of potassium chloride, 0.05% of magnesium sulfate, 0.2% of sodium nitrate and 0.35% of calcium carbonate; pH=7.0) and subjected to a shake culturing at 27° C. for 3 days to give a seed culture liquid.

The seed culture liquid (300 ml) was inoculated to a 30 liter jar fermentor containing 15 liters of fermentation medium (the same medium as the seed culture) and subjected to a stirring culture with aeration at 28° C. for 2 days (aeration: 15 liters per minute; stirring speed: 500 rpm). The culture liquid (70 liters) obtained here was filtered to separate from mycelia.

(2) (Extraction; Purification of the Fraction D)

The culture filtrate (70 liters) obtained in the above operation was extracted with 70 liters of ethyl acetate twice. The extracts were combined, the solvent was evaporated therefrom in vacuo, and 5.7 g of the residue was obtained. To this was added 4 liters of mixture of chloroform and water (1:1) and subjected to partition. The chloroform layer was taken and the solvent was removed in vacuo to give 3.2 g of the residue. The residue was subjected to a silica gel chromatography and eluted first with chloroform and then with a mixture of methanol and chloroform (2%→20%). Fractions containing active substances were collected, the solvent evaporated therefrom in vacuo, and 1.1 g of crude fraction containing active substances was obtained. This was treated with 200 ml of ethyl acetate containing 2 g of activated charcoal (Darco G-60), ethyl acetate was evaporated in vacuo, then subjected to a silica gel column charomatography once again, eluted with a 1:1 mixture of n-hexane and ethyl acetate, and the solvent was evaporated in vacuo to give 200 mg of SEN-366-D.

Its ir spectra are given in FIG. 5. $^1$H nmr spectra are shown in FIG. 15.

(3) (Manufacture of SEN-366-A$_1$ to A$_4$)

One gram of SEN-366-D obtained by the same way as above was dissolved in 3 ml of pyridine, 2 ml of acetic anhydride was added, and the mixture was stirred at room temperature for 3 hours. After the reaction, 50 ml of water was added and extracted with 50 ml of ethyl acetate twice. The ethyl acetate layer was washed with water, dried over anhydrous sodium sulfate, and ethyl acetate and pyridine were removed tehrefrom in vacuo. The residue (1.05 g) was subjected to a silica gel column chromatography and eluted with a 2:1 mixture of n-hexane and ethyl acetate to give four kinds of acetyl derivatives of SEN-366-D, i.e. SEN-366-A$_1$, SEN-366-A$_2$, SEN-366-A$_3$ and SEN-366-A$_4$, in 50, 65, 120 and 250 mg yields, respectively.

(4) (Manufacture of SEN-366-D$_1$, D$_3$)

SEN-366-A$_3$ (400 mg) obtained by the same way as before was added to 5 ml of 0.1N sodium hydroxide, the mixture was warmed at 50° C. and stirred for 1 hour. After hydrolysis, it was extracted with 50 ml of ether twice and ether was evaporated in vacuo to give 250 mg of the residue. The residue was subjected to a silica gel column chromatography and eluted with a 1:1 mixture of n-hexane and ethyl acetate to give 190 mg of olefinic compound of SEN-366-D. Its ir spectra are given in FIG. 6; $^1$H nmr spectra in FIG. 15; and uv spectra in FIG. 9.

(5) (Manufacture of SEN-366-D$_2$, D$_4$)

SEN-366-D (2.5 g) obtained by the same way as before was dissolved in 25 ml of ethanol, 300 mg of palladium carbon (5%) was added, and hydrogen gas was added thereto with stirring. Reduced product of SEN-366-D was obtained quantitatively (2.43 g). Its ir spectra, uv spectra and $^1$H nmr spectra are given in FIG. 7, FIG. 10 and FIG. 17, respectively.

(6) (Manufacture of benzoyl compound (SEN-366-B$_1$ to B$_4$)).

SEN-366-D (1 g) obtained by the same way as before was dissolved in 5 ml of pyridine, 2.5 g of benzoic anhydride was added, and the mixture was stirred at 80° C. for 4 hours. After the reaction, 100 ml of water was added and extracted with 100 ml of ethyl acetate twice. The ethyl acetate layer was washed with water, dried over anhydrous sodium sulfate, and ethyl acetate and pyridine were evaporated therefrom in vacuo. The resulting residue (3.17 g) was extracted with 100 ml of petroleum ether twice, the solvent was evaporated therefrom, the residue (2.75 g) was subjected to a silica gel column chromatography, and eluted with a 2:1 mixture of n-hexane and ethyl acetate to give 4 kinds of benzoyl compounds of SEN-366-D, i.e. SEN-366-B$_1$, SEN-366-B$_2$, SEN-366-B$_3$ and SEN-366-B$_4$, in 90, 60, 90 and 40 mg yields, respectively. Their $^1$H nmr spectra are given in FIG. 23 to FIG. 26. The ir spectra were measured using potassium bromide tablet. Both $^1$H nmr spectra and $^{13}$C nmr spectra were measured in CDCL$_3$ using TMS as internal standard. The uv spectra were measured by dissolving the substance in methanol.

(7) (Manufacture of butyryl compounds (SEN-366-BT$_1$ to BT$_4$)).

SEN-366-D (1 g) obtained by the same way as above was dissolved in 3 ml of pyridine, 400 mg of n-butyryl chloride was added, and the mixture was stirred at room temperature for 20 minutes. After the reaction, the same operation as in the above (6) was conducted to give 4 kinds of n-butyryl compounds of SEN-366-D, i.e. SEN-366-BT$_1$, SEN-366-BT$_2$, SEN-366-BT$_3$ and SEN-366-BT$_4$, in 50, 40, 200 and 150 mg yield, respectively. Their thin layer chromatography (using silica gel: Merck Art 5554; developing solvent: 1:1 mixture of ethyl acetate and n-hexane) gave Rf values of 0.71, 0.67, 0.63 and 0.58, respectively. In the meanwhile, $[\alpha]_D^{24}$ values of SEN-366-BT$_3$ and SEN-366-BT$_4$ were found to be $-30.32$ (c=0.521) and $-138.07$ (c=0.562), respectively.

EXAMPLE 2

(Manufacture of SEN-366-P)

Fresh wet mycelia (1.8 kg) obtained by the same way as in (1) of Example 1 was extracted with 2 liters of acetone twice and concentrated in vacuo. The resulting residue (35 g) was subjected to a silica gel column chromatography and eluted with a 1:1 mixture of n-hexane and ethyl acetate to give 150 mg of SEN-366-P. Its ir spectra and $^1$H nmr spectra are given in FIG. 8 and FIG. 18, respectively.

EXAMPLE 3

(Conversion of SEN-366-P to olefinic compound of SEN-366-D)

(1) Conversion of heating treatment of SEN-366-P to olefinic compound of SEN-366-D.

An aqueous solution (10 ml) containing 2.8 mg of SEN-366-P obtained by the same way as in Example 2 was heated in a boiling water (98°–100° C.) for 20 minutes and extracted with 10 ml ethyl acetate twice. The ethyl acetate layer was dried over anhydrous sodium sulfate and the ethyl acetate was evaporated in vacuo to give 2.2 mg of olefinic compound of SEN-366-D.

(2) (Conversion to olefinic compound of SEN-366-D by heating traatment of the culture liquid)

The culture liquid (10 liters) obtained by the same way as in (1) of Example 1 was heated at 92°–95° C. for 20 minutes, cooled, and the bacterial body was removed by filtration. The filtrate was extracted with 5 liters of ethyl acetate twice and concentrated in vacuo to give 1.3 g of the residue. This was similarly treated as in (2) of Example 1 to give 100 mg of olefinic compound of SEN-366-D.

When the same culture liquid was treated as same as in (2) of Example 1 without the heating treatment, 15 mg of SEN-366-D was obtained.

Compounds of formula (V) include the compounds listed in the following Table. In the Table, SEN-366-CB's are compounds of formula (V) in which R$^5$ is p-chlorobenzoyl; SEN-366-M's are those in which R$^5$ is methyl; SEN-366-E's are those in which R$^5$ is ethyl; and SEN-366-L's are those in which Y is =C=O.

| COMPOUNDS OF FORMULA V | | |
|---|---|---|
| | Orientation of OR$^5$ | === |
| SEN-366-CB$_1$ | α | double bond |
| SEN-366-CB$_2$ | α | single bond |
| SEN-366-CB$_3$ | β | double bond |
| SEN-366-CB$_4$ | β | single bond |
| SEN-366-M$_1$ | α | double bond |
| SEN-366-M$_2$ | α | single bond |
| SEN-366-M$_3$ | β | double bond |
| SEN-366-M$_4$ | β | single bond |
| SEN-366-E$_1$ | α | double bond |
| SEN-366-E$_2$ | α | single bond |
| SEN-366-E$_3$ | β | double bond |
| SEN-366-E$_4$ | β | single bond |
| SEN-366-L$_1$ | — | double bond |

| COMPOUNDS OF FORMULA V | | |
|---|---|---|
| | Orientation of $OR^5$ | $=$ |
| SEN-366-L$_2$ | — | single bond |

The SEN-366-E and SEN-366-M compounds may be obtained by alkylating SEN-366-D. The alkylation can utilize a method used in the reaction of sugars, i.e. O-alkylation of hydroxy group of anomeric carbon. For example, such an object can be achieved by the reaction with lower alcohols in the presence of acid catalysts such as mineral acids, Lewis acid, cation exchanger, etc. and the use of Lewis acid is preferred.

When the alkylated SEN-366-D as obtained above is purified by silica gel chromatography and recrystallized, four alkylated products are obtained. Thus, from the methylated SEN-366-D are obtained SEN-366-M$_1$, SEN-366-M$_2$, SEN-366-M$_3$ and SEN-366-M$_4$ and, from the ethylated SEN-366-D are obtained SEN-366-E$_1$, SEN-366-E$_2$, SEN-366-E$_3$ and SEN-366-E$_4$.

SEN-366-D may also be arylcarbonylated by conventional means. In this arylcarbonylation, the known esterification reactions may be utilized. Thus, for example, an acid anhydride or acid halide may be used solely or jointly with a suitable catalyst. When SEN-366-D is arylcarbonated as such, four kinds of arylcarbonylated substances are obtained. For example, para-chlorobenzoylation gives SEN-366-CB$_1$, SEN-366-CB$_2$, SEN-366-CB$_3$ and SEN-366-CB$_4$.

Ketones can be manufactured starting from SEN-366-D. Manufacture of such ketones is carried out by oxidation of the hydroxyl group at anomeric carbon position and, as to a method of oxidation, conventional means can be applied. They are, for example, direct oxidation using dimethyl sulfoxide, oxidation with activated dimethyl sulfoxide using dimethyl sulfoxide and dicyclohexylcarbodiimide, and the like. Oxidation using silver compounds such as silver oxide, silver carbonate, silver nitrate, etc. is especially preferred.

Properties of the compounds of the present invention are illustrated as hereunder.

(Physical and Chemical Properties)

(1) SEN-366-CB:

| (1) SEN-366-CB: | | | |
|---|---|---|---|
| | M.p. | $R_f$ | Specific Rotary Power $[\alpha]_D^{25}$ in CHCl$_3$ |
| SEN-366-CB$_1$ | 93–95° C. | 0.75 | −53.1 (c = 0.513) |
| SEN-366-CB$_2$ | 112–114 | 0.70 | −145.1 (c = 0.500) |
| SEN-366-CB$_3$ | 91–93 | 0.62 | −58.3 (c = 0.529) |
| SEN-366-CB$_4$ | 110–112 | 0.57 | −136.5 (c = 0.532) |

$R_f$ values: Thin layer chromatography (silica gel; Art 5554 (Merck)). Developer: n-hexane/ethyl acetate (1:1)

Elementary analysis: SEN-366-CB$_1$, SEN-366-CB$_3$ (C$_{25}$H$_{31}$O$_8$Cl) MW 494.5. Calcd (%) C: 60.67, H: 6.31, Cl: 7.16, Found (%) C: 60.42, H: 6.41, Cl: 7.24, (CB$_1$), C: 60.40, H: 6.45, Cl: 7.38 (CB$_3$).

SEN-366-CB$_2$, SEN-366-CB$_4$ (C$_{25}$H$_{33}$O$_8$Cl) MW 496.5. Calcd (%) C: 60.42, H: 6.69, Cl: 7.13, Found (%) C: 60.32, H: 6.68, Cl: 7.01 (CB$_2$), C: 60.14, H: 6.58, Cl: 6.91 (CB$_4$).

| SEN-366-M | | | |
|---|---|---|---|
| | M.p. (°C.) | $R_f$ | $[\alpha]_D^{25}$ in CHCl$_3$ |
| SEN-366-M$_1$ | (oily) | 0.62 | −70.54 (c = 0.550) |
| SEN-366-M$_2$ | 91~93 | 0.58 | −193.50 (c = 0.475) |
| SEN-366-M$_3$ | (oily) | 0.54 | −56.21 (c = 0.429) |
| SEN-366-M$_4$ | 91~93 | 0.51 | −173.52 (c = 0.441) |

$R_f$ values: Thin layer chromatography (Silica gel; Art 5554, of Merck). Developer: n-hexane/ethyl acetate (1:1)

Elementary analysis: SEN-366-M$_1$, SEN-366-M$_3$ (C$_{19}$H$_{30}$O$_7$) MW 370. Calcd (%) C: 61.60 H: 8.16, Found (%) C: 61.35, H: 8.31 (M$_1$), C: 61.33, H: 8.28 (M$_3$).

SEN-366-M$_2$, SEN-366-M$_4$ (C$_{19}$H$_{32}$O$_7$) MW 372. Calcd (%) C: 61.27, H: 8.66, Found (%) C: 61.09, H: 8.81 (M$_2$), C: 61.20, H: 8.79 (M$_4$).

| SEN-366-E | | | |
|---|---|---|---|
| | M.p. (°C.) | $R_f$ | $[\alpha]_D^{25}$ in CHCl$_3$ |
| SEN-366-E$_1$ | (oily) | 0.79 | −53.1 (c = 0.330) |
| SEN-366-E$_2$ | 42~43 | 0.74 | −145.2 (c = 0.500) |
| SEN-366-E$_3$ | (oily) | 0.69 | −41.3 (c = 0.420) |
| SEN-366-E$_4$ | 42~43 | 0.66 | −126.7 (c = 0.380) |

$R_f$ values: Thin layer chromatography (silica gel; Art 5554, by Merck) Developer: n-hexane/ethyl acetate (1:1)

Elementary analysis: SEN-366-E$_1$, SEN-366-E$_3$ (C$_{20}$H$_{32}$O$_7$) MW 384. Calcd (%) C: 62.48, H: 8.39, Found (%) C: 62.60, H: 8.21 (E$_1$), C: 62.63, H: 8.35 (E$_3$).

SEN-366-E$_2$, SEN-366-E$_4$ (C$_{20}$H$_{34}$O$_7$) MW 386. Calcd (%) C: 62.15, H: 8.87, Found (%) C: 61.98, H: 8.99 (E$_2$), C: 62.07, H: 8.92 (E$_4$).

| SEN-366-L | | | |
|---|---|---|---|
| | M.p. (°C.) | $R_f$ | $[\alpha]_D^{25}$ in CHCl$_3$ |
| SEN-366-L$_1$ | 155~156 | 0.75 | −41.33 (c = 0.300) |
| SEN-366-L$_2$ | 135~136 | 0.75 | −208.81 (c = 0.885) |

$R_f$ values: Thin layer chromatography (silica gel; Art 554 of Merck) Developer: CHCl$_3$/MeOH (25:1)

Elementary Analysis: SEN-366-L$_1$ (C$_{18}$H$_{26}$O$_7$) MW 354 Calcd (%) C: 61.00, H: 7.40, Found (%) C: 61.13, H: 7.26.

SEN-366-L$_2$ (C$_{18}$H$_{26}$O$_7$) MW 356. Calcd (%) C: 60.66, H: 7.92, Found (%) C: 60.42, H: 7.76.

Biological properties of the following compounds were determined by the method discussed above and are set forth in Table 2.

TABLE 2

| | IC$_{50}$ (μg/ml) | | |
|---|---|---|---|
| SEN-366 | Collagen 10 μg/ml | ADP 5 μM | AA 150 μM |
| CB$_1$ | 0.06 | 0.30 | 1.1 |
| CB$_2$ | 1.0 | 3.2 | 6.2 |
| CB$_3$ | 0.053 | 0.29 | 0.68 |
| CB$_4$ | 1.7 | 4.2 | 5< |
| M$_1$ | 5.5 | 17.0 | 29.0 |
| M$_2$ | 16.3 | 55.0 | 42.0 |
| M$_3$ | 5.2 | 15.0 | 25.0 |
| M$_4$ | 18.0 | 53.0 | 47.0 |
| E$_1$ | 2.0 | 7.2 | 10.3 |
| E$_2$ | 22.1 | 100< | 52.0 |
| E$_3$ | 4.4 | 12.4 | 14.0 |
| E$_4$ | 16.5 | 100< | 65.0 |

TABLE 2-continued

| SEN-366 | IC$_{50}$ (μg/ml) | | |
|---|---|---|---|
| | Collagen 10 μg/ml | ADP 5 μM | AA 150 μM |
| L$_1$ | 5.0 | 12.0 | 27.0 |
| L$_2$ | 48.0 | 50.0 | 100< |

It has been confirmed that the compounds of the present invention have very low toxicity. For example, the LD$_{50}$ values of SEN-366-CB to mice are not less than 500 mg/kg and not less than 100 mg/kg by oral administration and by intraperitoneal injection, respectively.

EXAMPLE 4

Manufacture of SEN-366-CB$_1$ to CB$_4$.

SEN-366-D (200 mg) obtained from Example 1 was dissolved in 1.0 ml of pyridine, 150 mg of p-chlorobenzoyl chloride was added, and the mixture was stirred at room temperature for 30 minutes. After the reaction, distilled water (50 ml) was added thereto and the mixture was extracted with 50 ml of ethyl acetate twice. The ethyl acetate layer was washed with water, dried over anhydrous sodium sulfate, and ethyl acetate and pyridne were evaporated therefrom in vacuo. The residue (300 mg) was subjected to a silica gel column chromatography and eluted with a 2:1 mixture of n-hexane and ethyl acetate to give 4 kinds of SEN-366-D p-chlorobenzoyl compounds, i.e. SEN-366-CB$_1$, SEN-366-CB$_2$, SEN-366-CB$_3$ and SEN-366-CB$_4$ in 10, 15, 10 and 12 mg yields, respectively.

EXAMPLE 5

Manufacture of SEN-366-M$_1$ to M$_4$.

SEN-366-D (800 mg) obtained by the above method was dissolved in 4.0 ml of anhydrous methanol, 400 mg of anhydrous magnesium sulfate was added thereto, and the mixture was heated to reflux for 3 hours. After the reaction, insoluble matters were removed by filtration. The filtrate was evaporated to dryness in vacuo. The residue (750 mg) was subjected to a silica gel column chromatography and eluted with a 2:1 mixture of n-hexane and ethyl acetate to give 4 kinds of methyl ethers of SEN-366-D, i.e. SEN366-M$_1$, SEN-366-M$_2$, SEN-366-M$_3$ and SEN-366-M$_4$ in 15, 26, 10 and 10 mg yields, respectively.

EXAMPLE 6

Manufacture of SEN-366-E$_1$ to E$_4$.

SEN-366-D (300 mg) obtained in the above method was dissolved in 2.0 ml of methanol, 150 mg of anhydrous magnesium sulfate was added, and the mixture was heated to reflux for 2 hours. After the reaction, insoluble matters were removed by filtration. The filtrate was evaporated to dryness in vacuo. The residue (290 mg) was subjected to a silica gel column chromatography and eluted with a 2:1 mixture of n-hexane and ethyl acetate to give 4 kinds of ethyl ethers of SEN-366-D, i.e. SEN-366-E$_1$, SEN-366-E$_2$, SEN-366-E$_3$ and SEN-366-E$_4$ in 10, 25, 10, and 20 mg yields, respectively.

EXAMPLE 7A

Manufacture of reduced compounds and olefinic compounds of SEN-366-D.

(1) SEN-366-D (1 g) obtained in the above method was dissolved in 3 ml of pyridine, 2 ml of acetic anhydride was added, and the mixture was stirred at room temperature for 3 hours. After the reaction, 50 ml of water was added thereto and the mixture was extracted with 50 ml of ethyl acetate twice. The ethyl acetate layer was washed with water, dried over anhydrous sodium sulfate, and ethyl acetate and pyridine were evaporated in vacuo. The residue (1.05 g) was subjected to a silica gel column chromatography and eluted with a 2:1 mixture of n-hexane and ethyl acetate to give 4 kinds of acetyl compounds of SEN-366-D, i.e. SEN-366-A$_1$, SEN-366-A$_2$, SEN-366-A$_3$ and SEN-366-A$_4$ in 50, 65, 120 and 250 mg yields, respectively.

(2) SEN-366-A$_3$ (400 mg) obtained by the same way as above was added to 5 ml of 0.1N sodium hydroixde, the mixture was warmed at 50° C., and stirred for 1 hour. After it was hydrolyzed, it was extracted with 50 ml of ether twice, ether was evaporated in vacuo from the extract, and 250 mg of residue was obtained. The residue was subjected to a silica gel column chromatography and eluted with a 1:1 mixture of n-hexane and ethyl acetate to give 190 mg of olefinic compound of SEN-366-D.

(3) SEN-366-D (2.5 g) obtained by the same method as above was dissolved in 25 ml of ethanol, 300 mg of palladium-carbon (5%) was added, and hydrogen gas was added thereto with stirring. Reduced SEN-366-D only was obtained quantitatively (2.43 g).

EXAMPLE 7B

Manufacture of SEN-366-L$_1$.

Olefinic compound (100 mg) of SEN-366-D obtained by the above method was dissolved in 2.0 ml of benzene, 150 mg of silver oxide was added, and the mixture was heated to reflux for 1 hour. After the reaction, the mixture was filtered and the filtrate was evaporated to dryness in vacuo to give 80 mg of SEN-366-L$_1$.

EXAMPLE 8

Manufacture of SEN-366-L$_2$.

Reduced product (100 mg) of SEN-366-D obtained by the above method was dissolved in 2.0 ml of benzene, 150 mg of silver oxide was added, and the mixture was heated to reflux for 1 hour. After the reaction, the mixture was filtered and the filtrate was evaporated in vacuo to remove benzene therefrom whereupon 80 mg of SEN-366-L$_2$ was obtained.

As stated above, SEN-366-F is obtained directly from the culturing of the microorganism. When SEN-366-F is subjected to column chromatography, it can be separated into the following two substances.

Olefinic compounds of SEN-366-F: The compound of general formula (VIII) where $===$ is a double bond, Y is $=CHOR^8$ and $R^8$ is hydrogen is named SEN-366-F$_0$ and, among it, the compound wherein the orientation of OR$^8$ is alpha is called SEN-366-F$_1$ and that wherein the orientation of OR$^8$ is beta is called SEN-366-F$_3$.

Reduced compounds of SEN-366-F: The compound of general formula (VIII) where $===$ is a single bond, Y is $=CHOR^8$ and $R^8$ is hydrogen is named SEN-366-F$_H$ and, among it, the compound wherein the orientation of OR$^8$ is alph is called SEN-366-F$_2$ and that wherein the orientation of OR$^8$ is beta is called SEN-366-F$_4$.

SEN-366-F and derivatives thereof have low toxicity and exhibit strong platelet aggregation inhibiting action. Thus, as fully described later under biological properties, SEN-366-F and derivatives thereof markedly inhibit the platelet aggregation of rats in which adenosine-5'-diphosphate (ADP), arachidonic acid (AA) or collagen is used as platelet aggregation inducers. Accordingly, those substances are useful as pharmaceuticals for prevention and therapy of the above given thrombosis.

SEN-366-F-A is a compound (VIII) in which Y is =CHOR$^8$ and R$^8$ is acetyl; SEN-366-F-BT is a compound (VIII) in which Y is =CHOR$^8$ and R$^8$ is butyryl; SEN-366-F-B is a compound (VIII) in which Y is =CHOR$^8$ and R$^8$ is benzoyl; SEN-366-F-CB is a compound (VIII) in which Y is =CHOR$^8$ and R$^8$ is p-chlorobenzoyl; SEN-366F-M is a compound (VIII) in which Y is =CHOR$^8$ and R$^8$ is methyl; SEN-366-F-E is a compound (VIII) in which Y is =CHOR$^8$ and R$^8$ is ethyl; SEN-366-F-L is a compound (VIII) in which Y is =C=O.

There are four compounds in each of these compounds depending on the stereochemistry and the saturation of the pyran-3-one ring. The compounds in which OR$^8$ is alpha and === is a double bond are named SEN-366-F-A$_1$, BT$_1$, CB$_1$, M$_1$ and E$_1$, respectively; the compounds in which OR$^8$ is alpha and === is a single bond are named SEN-366-F-A$_2$, BT$_2$, B$_2$, CB$_2$, M$_2$, and E$_2$, respectively; the compounds in which OR$^8$ is beta and === is a double bond are named SEN-366-F-A$_3$, BT$_3$, B$_3$, CB$_3$, M$_3$, and E$_3$, respectively; and the compounds in which OR$^8$ is beta and === is a single bond are named SEN-366-F-A$_4$, BT$_4$, B$_4$, CB$_4$, M$_4$, and E$_4$, respectively.

The compounds where Y is =C=O and === is a double bond is named SEN-366-F-L$_0$ and the compound where Y is =C=O and === is a single bond is named SEN-366-F-L$_H$. SEN-366-F obtained from the microorganism, may be acylated or acylcarbonylated by conventional means. In such an acylation or arylcarbonylation, usual esterification reaction utilizing acid anhydride, acid halide, etc. with or without suitable solvent can be applied. When SEN-366-F is acetylated as such, four kinds of acetyl derivatives—SEN-366-F-A$_1$, SEN-366-F-A$_2$, SEN-366-F-A$_3$ and SEN-F-A$_4$ are obtained. When lower acyl derivative or arylcarbonyl derivative obtained as such is hydrolyzed by usual means, the following compounds, for example, are obtained. Thus, olefinic compound SEN-366-F$_0$ (a mixture of F$_1$ and F$_3$) from SEN-366-F-A$_1$ or from SEN-366-F-A$_3$; and reduced compound SEN-366-F$_H$ (a mixture of F$_2$ and F$_4$) from SEN-366-F-A$_2$ or from SEN-366-F-A$_4$.

When SEN-366-F or F$_0$ is subjected to a catalytic reduction, the reduced compound SEN-366-F$_H$ (a mixture of F$_2$ and F$_4$) is obtained.

SEN-366-F can be alkylated by conventional means. Said alkylation may be conducted by usual reaction which is applied for O-alkylation of hydroxyl group in anomeric carbon or the conventional method used in the reaction for sugars. The reaction with lower alcohol in the presence of acid catalysts such as mineral acids, Lewis acid, cation exchangers, etc. may also gives the desired alkylated products.

Manufacture of ketone substances starting from SEN-366-F is also possible. Manufacture of the ketone substances is done by oxidation of hydroxyl group of anomeric position carbon and can be conducted by conventional oxidation such as, for example, a direct oxidation using dimethyl sulfoxide or an oxidation with activated dimethyl sulfoxide using dimethyl sulfoxide and dicyclohexylcarbodiimide. Oxidation using silver compounds such as silver oxide, silver carbonate and silver nitrate is especially preferred.

In addition, SEN-366-F, SEN366-F$_0$ and SEN-366-F$_H$ can be manufactured by an acid decomposition of the previously isolated compound of the general formula IV (cf. Japanese Patent Application No. 222740/84):

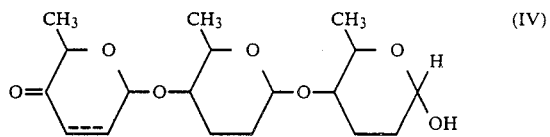

(in which  is a single or double bond) such as, for example, SEN-366-D (the compound IV where === is a single or double bond and is a mixture of alpha or beta-anomers), SEN-366-D$_0$ (the compound IV where === is a double bond and is a mixture of alpha- or beta-anomers), and SEN-366-D$_H$ (the compound IV where === is a single bond and is a mixture of alpha- or beta-anomers).

(Physical and Chemical Properties)

Properties of the compounds of the present invention are as follows:

| | 1 SEN-366-F-A | | |
|---|---|---|---|
| | M.p. (°C.) | Rf | Specific Rotary Power $[\alpha]_D^{24}$ in CHCl$_3$ |
| SEN-366-F-A$_1$ | (oily) | 0.65 | −35.0 (c = 0.44) |
| SEN-366-F-A$_2$ | 53~55 | 0.64 | −188.2 (c = 0.80) |
| SEN-366-F-A$_3$ | (oily) | 0.59 | 53.33 (c = 0.62) |
| SEN-366-F-A$_4$ | 43~46 | 0.59 | −127.2 (c = 0.70) |

Rf: Thin layer chromatography: (Kieselgel 60F254) Developer; n-hexane/AcOEt (1:1)

Elementary Analysis: SEN-366-F-A$_1$, SEN-366-F-A$_3$ (C$_{14}$H$_{20}$O$_6$). Calcd (%) C: 59.14, H: 7.09, Found (%) C: 59.43, H: 7.02 (F-A$_1$), C: 59.29, H: 7.08 (F-A$_3$).

SEN-366-F-A$_2$, SEN-366-F-A$_4$ (C$_{14}$H$_{22}$O$_6$). Calcd (%) C: 58.73, H: 7.75, Found (%) C: 58.96, H: 7.74 (F-A$_2$), C: 58.76, H: 7.83 (F-A$_4$).

NMR (CDCl$_3$) δ:
SEN-366-F-A$_1$: 1.22 (3H, d), 1.39 (3H, d), 2.10 (3H, s), 3.68 (1H, br), 4.05 (1H, dq), 4.58 (1H, q), 5.25 (1H, d), 6.10 (1H, d), 6.15 (1H, br), 6.87 (1H, dd).

SEN-366-F-A$_2$: 1.20 (3H, d), 1.28 (3H, d), 2.10 (3H, s), 3.65 (1H, br), 4.03 (1H, q), 4.33 (1H, q), 5.07 (1H, t), 6.16 (1H, br),

SEN-366-F-A$_3$: 1.29 (3H, d), 1.38 (3H, d), 2.09 (3H, s), 3.58 (1H, br), 3.79 (1H, dq), 4.59 (1H, q), 5.21 (1H, d), 5.71 (1H, dd), 6.08 (1H, d), 6.85 (1H, d)

SEN-366-F-A$_4$: 1.27 (3H, d), 1.28 (3H, d), 2.11 (3H, s), 3.55 (1H, br), 3.77 (1H, dq), 4.33 (1H, q), 5.05 (1H, t), 5.71 (1H, dd),

| | SEN-366-F-BT | | |
|---|---|---|---|
| | M.p. (°C.) | Rf | $[\alpha]_D^{24}$ in CHCl$_3$ |
| SEN-366-F-BT$_2$ | (oily) | 0.42 | −91.9 (c = 0.46) |
| SEN-366-F-BT$_4$ | 59~62 | 0.37 | −119.6 (c = 1.46) |

Rf: Thin layer-chromatography: (Kieselgel 60F254), Developer: n-hexane/AcOEt (2:1).

Elementary analysis: SEN-366-F-BT$_2$, SEN-366-F-BT$_4$. (C$_{16}$H$_{26}$O$_6$). Calcd (%) C: 61.13, H: 8.34, Found (%) C: 61.21, H: 8.33 (F-BT$_2$), C: 61.01, H: 8.24 (F-BT$_4$).

| SEN-366-F-B | | | |
|---|---|---|---|
| | Mp (°C.) | Rf | $[\alpha]_D^{24}$ in CHCl$_3$ |
| SEN-366-F-B$_2$ | 93~94 | 0.43 | −197.2 (c = 0.57) |
| SEN-366-F-B$_4$ | 131~132 | 0.38 | −112.5 (c = 0.53) |

Rf: Thin layer chromatography: Kieselgel 60F254), Developer: n-hexane/AcOEt (2:1).
Elementary Analysis: SEN-366-F-B$_2$, SEN-366-F-B$_4$ (C$_{19}$H$_{24}$O$_6$), Calcd (%) C: 65.50, H: 6.94, Found (%) C: 65.27, H: 6.99 (F-B$_2$), C: 65.49, H: 6.96 (F-B$_4$).

| SEN-366-F-CB | | | |
|---|---|---|---|
| | M.p. (°C.) | Rf | $[\alpha]_D^{24}$ in CHCl$_3$ |
| SEN-366-F-CB$_2$ | 129~131 | 0.43 | −178.6 (c = 0.49) |
| SEN-366-F-CB$_4$ | 136~138 | 0.37 | −90.8 (c = 0.78) |

Rf: Thin layer chromatography: (Kieselgel 60F254), Developer: n-hexane/AcOEt (2:1).
Elementary Analysis: SEN-366-F-CB$_2$, SEN-366-F-CB$_4$ (C$_{19}$H$_{23}$O$_6$Cl). Calcd (%) C: 59.61, H: 6.06, Found (%) C: 59.82, H: 6.07 (F-CB$_2$), C: 59.59, H: 6.05 (F-CB$_4$).

| SEN-366-F-M | | | |
|---|---|---|---|
| | M.p. (°C.) | Rf | $[\alpha]_D^{24}$ in CHCl$_3$ |
| SEN-366-F-M$_2$ | (oily) | 0.61 | −237.4 (c = 0.53) |
| SEN-366-F-M$_4$ | (oily) | 0.51 | −108.7 (c = 0.55) |

Rf: Thin layer chromatography: (Kieselgel 60F254) Developer; n-hexane/AcOEt (1:1).
Elementary Analysis: SEN-366-F-M$_2$, SEN-366-F-M$_4$ (C$_{13}$H$_{22}$O$_5$), Calcd (%) C: 60.44, H: 8.59, Found (%) C: 60.41, H: 8.58 (F-M$_2$), C: 60.59, H: 8.57 (F-M$_4$).

| SEN-366-F-E | | | |
|---|---|---|---|
| | M.p. (°C.) | Rf | $[\alpha]_D^{24}$ in CHCl$_3$ |
| SEN-366-F-E$_2$ | 53~56 | 0.42 | −251.1 (c = 0.77) |
| SEN-366-F-E$_4$ | (oily) | 0.36 | −116.9 (c = 0.45) |

Rf: Thin layer chromatography: (Kieselgel 60F254), Developer; n-hexane/AcOEt (2:1).
Elementary Analysis: SEN-366-F-E$_2$, SEN-366-F-E$_4$ (C$_{14}$H$_{24}$O$_5$), Calcd (%) C: 61.74, H: 8.88, Found (%) C: 61.79, H: 8.87 (F-E$_2$), C: 61.57, H: 8.86 (F-E$_4$).

| SEN-366-F-L | | | |
|---|---|---|---|
| | (°C.) | Rf | $[\alpha]_D^{24}$ in CHCl$_3$ |
| SEN-366-F-L$_H$ | 87~89 | 0.64 | −193.8 (c = 0.52) |

Rf: Thin layer chromatography: (Kieselgel 60F254), Developer, Chloroform/Methanol (25:1).
Elementary Analysis: SEN-366-F-L$_H$ (C$_{12}$H$_{18}$O$_5$), Calcd (%) C: 59.49, H: 7.49, Found (%) C: 59.73, H: 7.51.

(Biological Properties)
Biological properties of the compounds of the present invention are as follows:
Inhibitory Action against Platelet Aggregation:
(1) Materials and Method:
The sample is tested after dissolved in dimethyl sulfoxide. The preparation is conducted so as to make the final concentration of the solvent 1%. Dimethyl sulfoxide of the same concentration is used as a control. As to inducers for platelet aggregation, ADP (final concentration: 5 μM), AA (arachidonic acid) (final concentration: 150 μM) and collagen (final concentration: 10 μg/ml) are used.

(2) Preparation of platelet:
Blood is taken from total neck artery of male rabbits of 2.0–2.5 kg body weight. To the blood is added 1/10 volume of 3.8% citric acid solution, the mixture is gently stirred, centrifuged 1300×g for 2 minutes, and the resulting supernatant liquid is used as plasma with abundant platelet (hereinafter abbreviated as PRP). The precipitate is further centrifuged at 1600×g for 10 minutes and the resulting supernatant liquid is used as plasma with poor platelet (hereinafter abbreviated as PPP).

(3) Method for Measuring Aggregation Power:
A measuring apparatus for platelet aggregation is used and the changes in absorbancy by the aggregation with an elapse of time are recorded.
Thus, 200 microliters of PRP is taken, its difference between PPP is adjusted to a certain value, then 25 microliters of control solution or test solution is added, the mixture is stirred (1000 rpm) for 1 minute, 25 microliters of aggregation inducer is added, and the changes in absorbancy are recorded. The inhibitory ratio is calculated from the following expression from the maximum aggregation ratio of the control (A in %) and that of the test solution (B in %):

$$\text{Inhibitory Ratio (\%)} = \left(1 - \frac{B}{A}\right) \times 100$$

Inhibitory ratios with varied test solution concentrations are calculated and the IC$_{50}$ (50% inhibitory concentration) is calculated therefrom. The result with the representative compounds of the present invention is given in Table 3.

TABLE 3

| | IC$_{50}$ (μg/ml) | | |
|---|---|---|---|
| | Collagen | ADP | AA |
| SEN-366 | 10 μg/ml | 5 μM | 150 μM |
| F$_0$ | 1.5 | 9.3 | 3.4 |

EXAMPLE 9

Manufacture of SEN-366-F, SEN-366-F$_0$ and SEN-366-F$_H$.
(1) Culture.
From a slant culture of Streptomyces sp. SEN-366, said culture was planted on 100 ml of seed medium (containing 2% starch, 1% soybean powder, 0.5% sodium chloride, 0.05% potassium chloride, 0.05% magnesium sulfate, 0.2% sodium nitrate and 0.35% calcium carbonate; pH 7.0) in sterilized 500 ml Erlenmeyer flask and then subjected to a shake culture at 27° C. for 3 days to give seed culture liquid.
This seed culture liquid (300 ml) was incubated in a 30 liter jar fermentor in which 15 liters of fermentation medium (the same as the seed medium) and subjected to culture with aeration (15 liters/min) and stirring (500 rpm) at 28° C. for 2 days. The resulting culture liquid (70 liters) was separated from bacterial body by filtration.

(2) Isolation and purification of fraction F followed to an extraction.

The culture filtrate (70 liters) obtained in the above operation was extracted with 70 liters of ethyl acetate twice. The combined extracts were evaporated in vacuo to remove the solvent to give 8.3 grams of residue. To this was added 6 liters of a 1:1 mixture of chloroform and water and subjected to partition. The chloroform layer was taken, the solvent was evaporated therefrom, and 4.7 g of residue was obtained. This residue was subjected to a silica gel column chromatography and eluted first with chloroform and then with a mixture of methanol and chloroform (2%→20%). Fractions containing active substances were collected, the solvent was evaporated therefrom in vacuo, and 1.6 g of crude active substances fraction was obtained. This was treated with 300 ml of ethyl acetate containing 2 g of Darco G-60 (activated charcoal), ethyl acetate was evaporated therefrom in vacuo, then subjected to a silica gel column chromatography once again, and eluted with a 7:3 mixture of n-hexane and ethyl acetate followed by evaporating the solvent in vacuo to give 91 mg of SEN-366-F.

(3) Separation, isolation of $F_0$ and $F_H$ and purification.

SEN-366-F (1.0 g) obtained by the same way was subjected to a reversed phase column chromatography (Li Chrocrep RP 18) and eluted with a 25:75 mixture of acetonitrile and water to give 110 mg of SEN-366-$F_0$ and 720 mg of SEN-366-$F_H$. $^1$H nmr spectra of them are shown in FIG. 1 and in FIG. 2.

EXAMPLE 10

Manufacture of SEN-366-F-$A_1$ to $A_4$.

SEN-366-F (2.0 g) obtained by the same method in Example 9(2) was dissolved in 8 ml of pyridine, 10 ml of acetic anhydride was added, and the mixture was stirred at room temperature for 2 hours. After the reaction, 70 ml of water was added thereto and the mixture was extracted with 80 ml of ethyl acetate thrice. The ethyl acetate layer was washed with water, dried over anhydrous sodium sulfate, and the solvent was evaporated in vacuo. The residue (2.2 g) was subjected to a silica gel column chromatography and eluted with a 2:1 mixture of n-hexane and ethyl acetate to give four kinds of acetyl derivatives of SEN-366-F-A, i.e. SEN-366-F-$A_1$, SEN-366-F-$A_2$, SEN-366-F-$A_3$ and SEN-366-F-$A_4$, in 139, 204, 163 and 149 mg yields, respectively.

EXAMPLE 11

Manufacture of SEN-366-F-$BT_2$ and SEN-366-F-$BT_4$.

SEN-366-$F_H$ (1.0 g) obtained by the same way as in Example 9(3) was dissolved in 3 ml of pyridine, 1.1 g of butyl chloride was added, and the mixture was stirred at room temperature for 30 minutes. After the reaction, 40 ml of water was added and the mixture was extracted with 40 ml of ethyl acetate thrice. The ethyl acetate layer was washed with water, dried over anhydrous sodium sulfate and the solvent was evaporated therefrom in vacuo. The residue (2.1 g) was subjected to a silica gel column chromatography (n-hexane:ethyl acetate=2:1) and medium pressure column chromatography (n-hexane:ethyl acetate=4:1) to give two kinds of n-butyryl derivatives, i.e. SEN-366-F-$BT_2$ and SEN-366-$BT_4$, in 52 and 461 mg yields, respectively.

EXAMPLE 12

Manufacture of SEN-366-F-$B_2$ and SEN-

SEN-366-$F_H$ (1.1 g) obtained in the same way as Example 9(3) was dissolved in 5 ml of pyridine, 2 g of benzoic anhydride was added, and the mixture was stirred at 70° C. for 6 hours. After the reaction, 40 ml of water was added, and the mixture was extracted with 20 ml of diethyl ether for four times. The ether extract was dried, ether was evaporated therefrom in vacuo, and 3.8 g syrupy residue was obtained. The residue was purified by a silica gel column chromatography (n-hexane:ethyl acetate=2:1) to give 2 kinds of benzoyl compounds—SEN-366-F-$B_2$ and SEN-366-F-$B_4$—in 429 and 536 mg, respectively. Both were in needles.

EXAMPLE 13

Manufacture of SEN-366-F-$CB_2$ and SEN-366-F-$CB_4$.

SEN-366-$F_H$ (1.0 g) obtained by the same way as in Example 9(3) was dissolved in 4.0 ml pyridine, 0.8 ml p-chlorobenzoyl chloride added, stirred at room temperature for 1 hour, 30 ml distilled water added, and extracted with 30 ml diethyl ether for four times. The diethyl ether layer was washed with water, dried over anhydrous sodium sulfate, both diethyl ether and pyridine were evaporated in vacuo, the residue (1.2 g) subjected to a silica gel column chromatography, eluted with a 2:1 mixture of n-hexane and ethyl acetate and purified by further subjecting to a medium pressure column chromatography (eluting solvent: n-hexane/ethyl acetate=7/3) to give 2 kinds of p-chlorobenzoyl derivatives of SEN-366-F, i.e. SEN-366-F-$CB_2$ and SEN-366-F-$CB_4$, in 55 and 364 mg yields, respectively.

EXAMPLE 14

Manufacture of SEN-366-F-$M_2$ and SEN-366-F-$M_4$.

SEN-366-$F_H$ (1.0 g) obtained by the same way as in Example 9(3) was dissolved in 5.0 ml anhydrous methanol, 500 mg anhydrous magnesium sulfate added, heated to reflux for 2 hours, filtered to remove insoluble matters, the filtrate evaporated to dryness in vacuo, the residue (929 mg) subjected to a silica gel column chromatography, eluted with a 2:1 mixture of n-hexane and ethyl acetate, and purified by subjecting to a medium pressure column chromatography (eluting solvent is a 2:1 mixture of n-hexane and ethyl acetate) to give 2 kinds of methyl ethers of SEN-366-F, i.e. SEN-366-F-$M_2$ and SEN-366-F-$M_4$, in 395 and 100 mg yields, respectively.

EXAMPLE 15

Manufacture of SEN-366-F-$E_2$ and SEN-366-F-$E_4$.

SEN-366-$F_H$ (1.09 g) obtained by the same way as in Example 9(3) was dissolved in 5.0 ml of anhydrous methanol, 500 mg of anhydrous magnesium sulfate added, heated to reflux for 15 hours, filtered to remove insoluble matters, the filtrate evaporated to dryness in vacuo, the residue (872 mg) subjected to a silica gel column chromatography, and eluted with a 2:1 mixture of n-hexane and ethyl acetate to give two kinds of ethyl ether derivatives of SEN-366-F, i.e. SEN-366-F-$E_2$ and SEN-366-F-$E_4$, in 351 and 102 mg yields, respectively.

EXAMPLE 16

Manufacture of SEN-366-F-$L_H$.

SEN-366-F$_H$ (500 mg) obtained in the method of Example 9(3) was dissolved in 5.0 ml benzene, 700 mg silver oxide added, heated at 60° C. for 1 hour, filtered, benzene was removed from the filtrate in vacuo, and the residue recrystallized from ether-n-hexane to give 80 mg of SEN-366-F-L$_H$.

(2) Manufacture of SEN-366-A$_1$ to A$_4$.

SEN-366-D (1 g) obtained by the same way as above was dissolved in 3 ml of pyridine, 2 ml acetic anhydride added, stirred at room temperature for 3 hours, 50 ml water added, extracted with 50 ml ethyl acetate twice, the ethyl acetate layer washed with water, dried over anhydrous sodium sulfate, then ethyl acetate

EXAMPLE 17

To 520 grams of the olefinic compound SEN-366-D [Example 1(3)] was was added 10 ml of 0.1N hydrochloric acid, stirred at room temperature for one hour, neutralized with sodium hydroxide, extracted with 15 ml ethyl acetate thrice, the ethyl acetate layer was evaporated in vacuo, the residue subjected to a medium pressure column chromatography (silica gel), and eluted with a 3:7 mixture of ethyl acetate and n-hexane to give 91.4 mg oily SEN-366-F$_O$.

Compounds of formula (X)

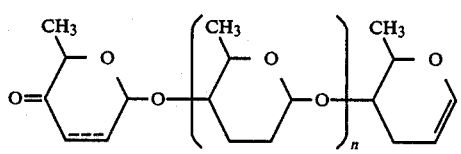
(X)

in which n is 0 or 1; and $\equiv\equiv\equiv$ is a single or double bond, may be prepared by dehydrating compound (XI):

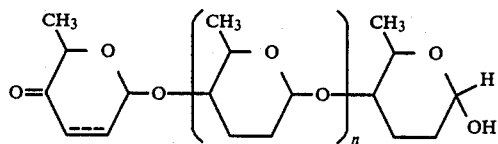
(XI)

in which n is 0 or 1; and $\equiv\equiv\equiv$ is a single or double bond.

There are alpha- and beta-anomers—or the compounds of the formula (XI) depending upon the steric orientation and both of them can be converted to the compounds (X) of the present invention. Compound (XI) includes compound (II) wherein R$^2$ is hydrogen and compound VIII wherein Y is =CHOR$^8$ and R$^8$ is hydrogen.

The compounds of the present invention represented by (X) are manufactured by a direct dehydration reaction of the compound (XI). For example, the compound (XI) is heated together with pyridine and phthalic anhydride to give (X).

Physical and chemical properties of representative compounds of the present invention are given in the following examples.

Biological properties of the compounds of the present invention are measured as already described in an earlier part of this specification. The result is given in Table 4.

TABLE 4

| Compound (Example Number) | IC$_{50}$ (μg/ml) Collagen 10 μg/ml | ADP 5 μM | AA 150 μM |
| --- | --- | --- | --- |
| 9 | 1.55 | 7.5 | 12.5 |

EXAMPLE 18

A compound (1 g) of the formula (XI) where $\equiv\equiv\equiv$ is a single bond and n=1 was dissolved in 3 ml of pyridine, 750 mg of phthalic anhydride was added, and the mixture was stirred at 70°-80° C. for 3 hours. After the reaction, 50 ml of water was added and the mixture was extracted with 50 ml of ethyl acetate twice. The ethyl acetate layer was washed with water, dried over anhydrous sodium sulfate, and the solvent was evaporated therefrom in vacuo. The residue (910 mg) was subjected to a silica gel column chromatography (Wakogel C-300), eluted with a 2:1 mixture of n-hexane and ethyl acetate and recrystallized from ether to give 265 mg of the compound (X) where $\equiv\equiv\equiv$ is a single bond and n is 1.

Optical rotary power: $[\alpha]_D^{24} = -242.83$ (c=0.691, CHCl$_3$). M.p. 86°-87° C. (colorless crystals). R$_f$ 0.72. Thin layer chromatography (Kieselgel 60F254). Developer is a 1:1 mixture of ethyl acetate and n-hexane.

Elementary analysis calculated for C$_{18}$H$_{28}$O$_6$: C 63.51, H 8.29; Found: C 63.38, H 8.40.

EXAMPLE 19

A compound (500 mg) of the formula (XI) in which $\equiv\equiv\equiv$ is a double bond and n=1 was dissolved in 2 ml pyridine, stirred at 70°-80° C. with 375 mg phthalic anhydride for 3 hours, 50 ml water added, extracted with 50 ml ethyl acetate twice, the ethyl acetate layer washed with water, dried over anhydrous sodium sulfate, evaporated in vacuo, the residue (470 mg) subjected to a silica gel column chromatography (Wakogel C-300), eluted with a 2:1 mixture of n-hexane and ethyl acetate, and recrystallized from ether to give 55 mg of (X) in which $\equiv\equiv\equiv$ is a double bond and n=1. Optical rotary power, $[\alpha]_D^{24} = -46.82$ (c=0.615, CHCl$_3$), M.p. 113°-115° C. (colorless crystals). Rf 0.76, thin layer chromatography (Kieselgel 60F254). Developer is a 1:1 mixture of ethyl acetate and n-hexane. Elementary analysis calculated for C$_{18}$H$_{26}$O$_6$: C 63.88, H 7.74; Found: C 63.61, H 7.82.

EXAMPLE 20

A compound of (XI) where $\equiv\equiv\equiv$ is a single bond and n=0 (1 g) was dissolved in 2 ml pyridine, 600 mg phthalic anhydride added, stirred at 70°-80° C. for 3 hours, 50 ml water added, extracted with 50 ml ethyl acetate twice, the ethyl acetate layer washed with water, dried over anhydrous sodium sulfate, the solvent evaporated in vacuo, the residue (760 mg) subjected to a silica gel column chromatography (Wakogel C-300) and eluted with a 2:1 mixture of n-hexane and ethyl acetate to give (X) where $\equiv\equiv\equiv$ is a single bond and n=0. The yield was 180 mg. Optical rotary power, $[\alpha]_D^{24} = -241.41$ (c=1.019, CHCl$_3$). Oil. Rf 0.75. Thin layer chromatography (Kieselgel 60F254). Developer is a 1:1 mixture of ethyl acetate and n-hexane. Elementary analysis calculated for C$_{12}$H$_{18}$O$_4$: C 63.70, H 8.02; Found: C 63.84. H 7.93.

Figure 1:
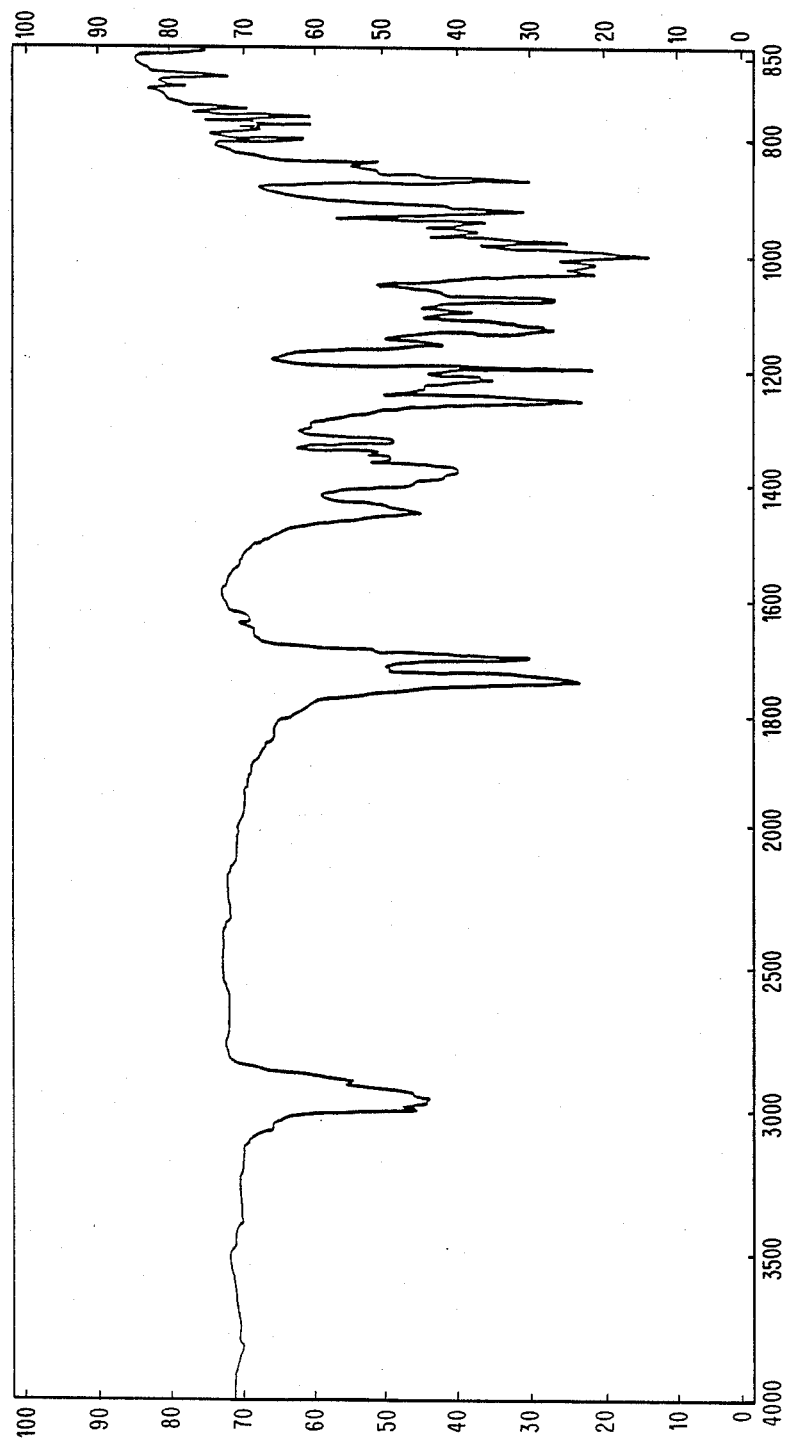
FIG. 1 shows ir spectra of SEN-366-A$_1$ of the present invention. The measuring condition is KBr disc. The ordinate is transmittances (%) and the abscissa is wave numbers (cm$^{-1}$).
Figure 2:
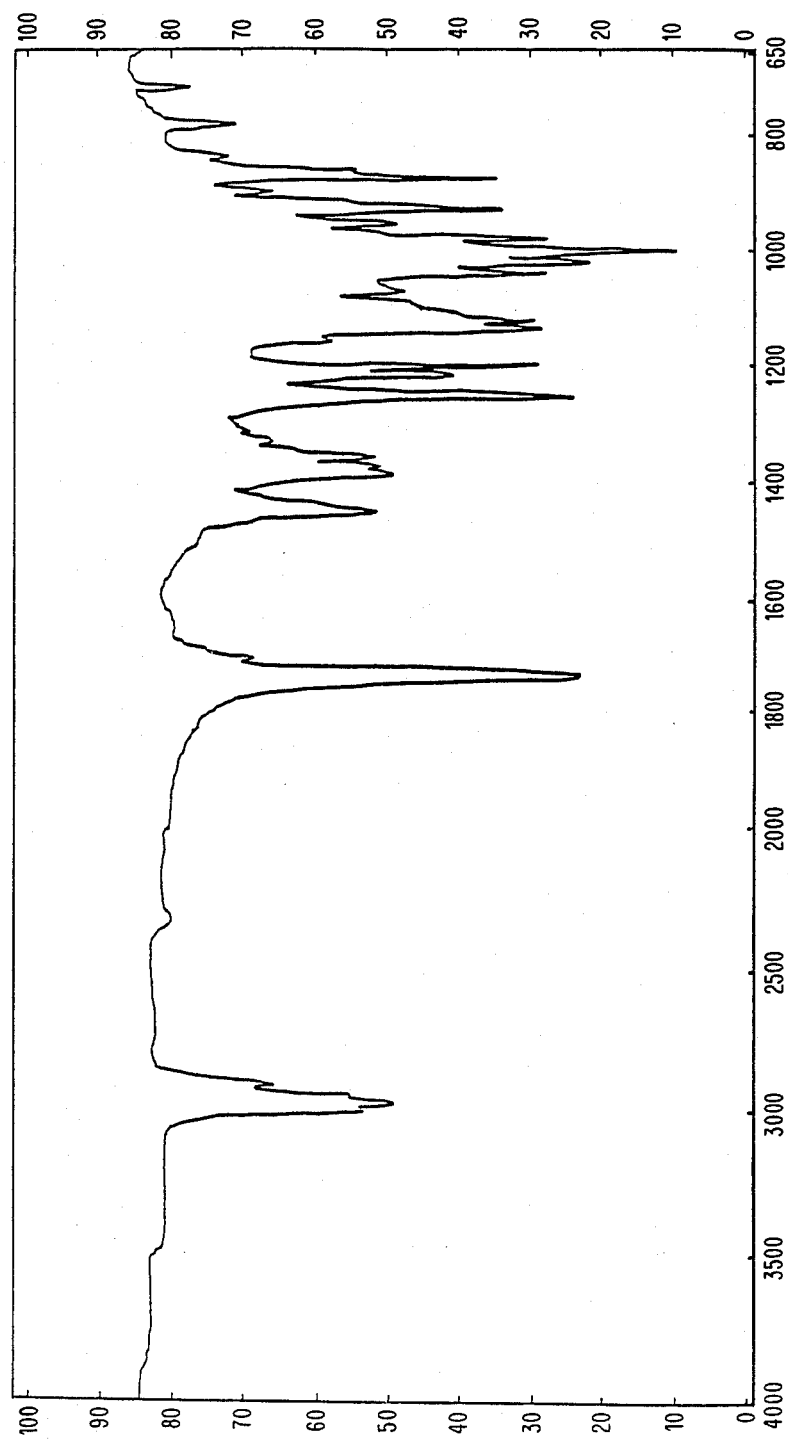
FIG. 2 shows ir spectra of SEN-366-A$_2$ of the present invention. The measuring condition is KBr disc. The ordinate is transmittances (%) and the abscissa is wave numbers (cm$^{-1}$).
Figure 3:
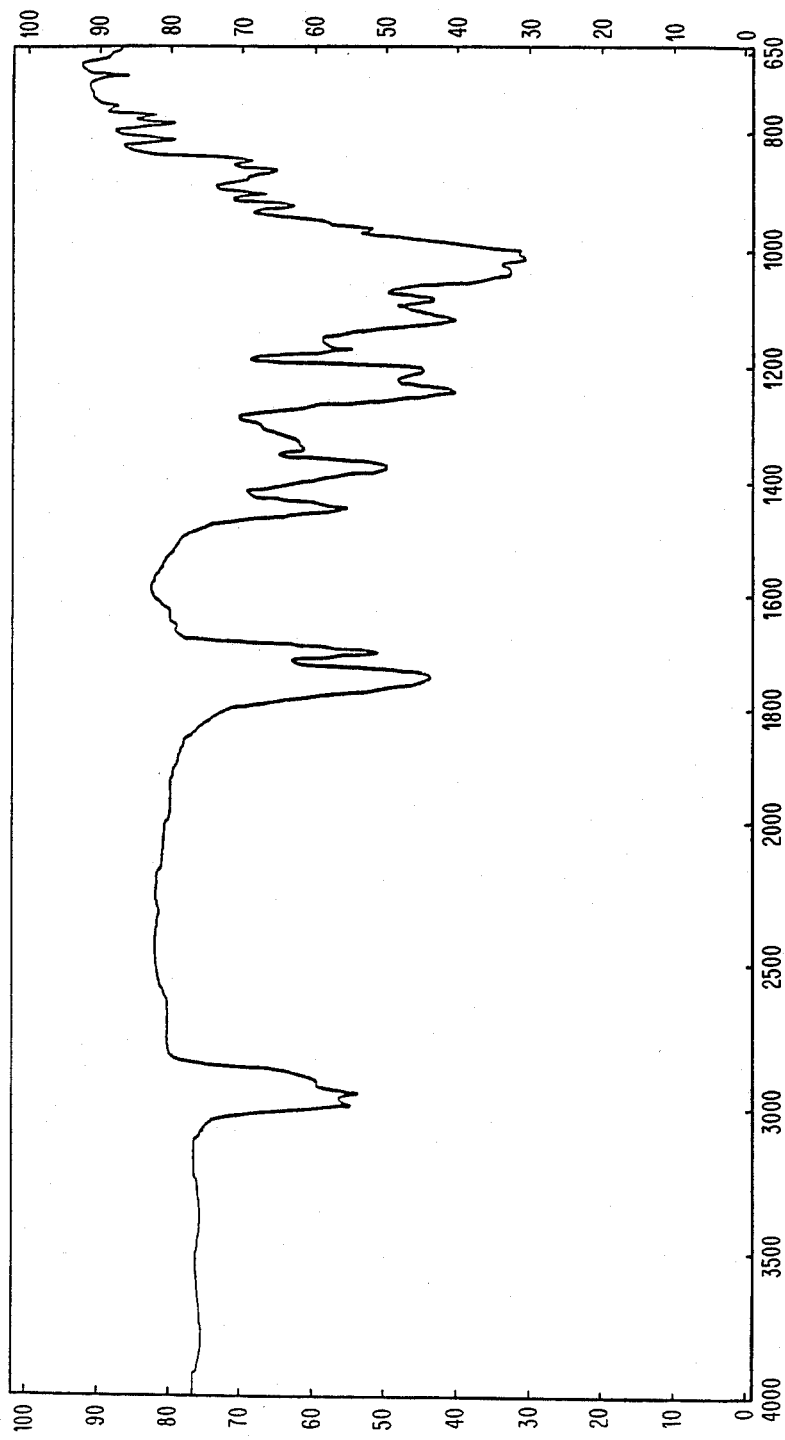
FIG. 3 shows ir spectra of SEN-366-A$_3$ of the present invention. The measuring condition is KBr disc. The ordinate is transmittances (%) and the abscissa is wave numbers (cm$^{-1}$).
Figure 4:
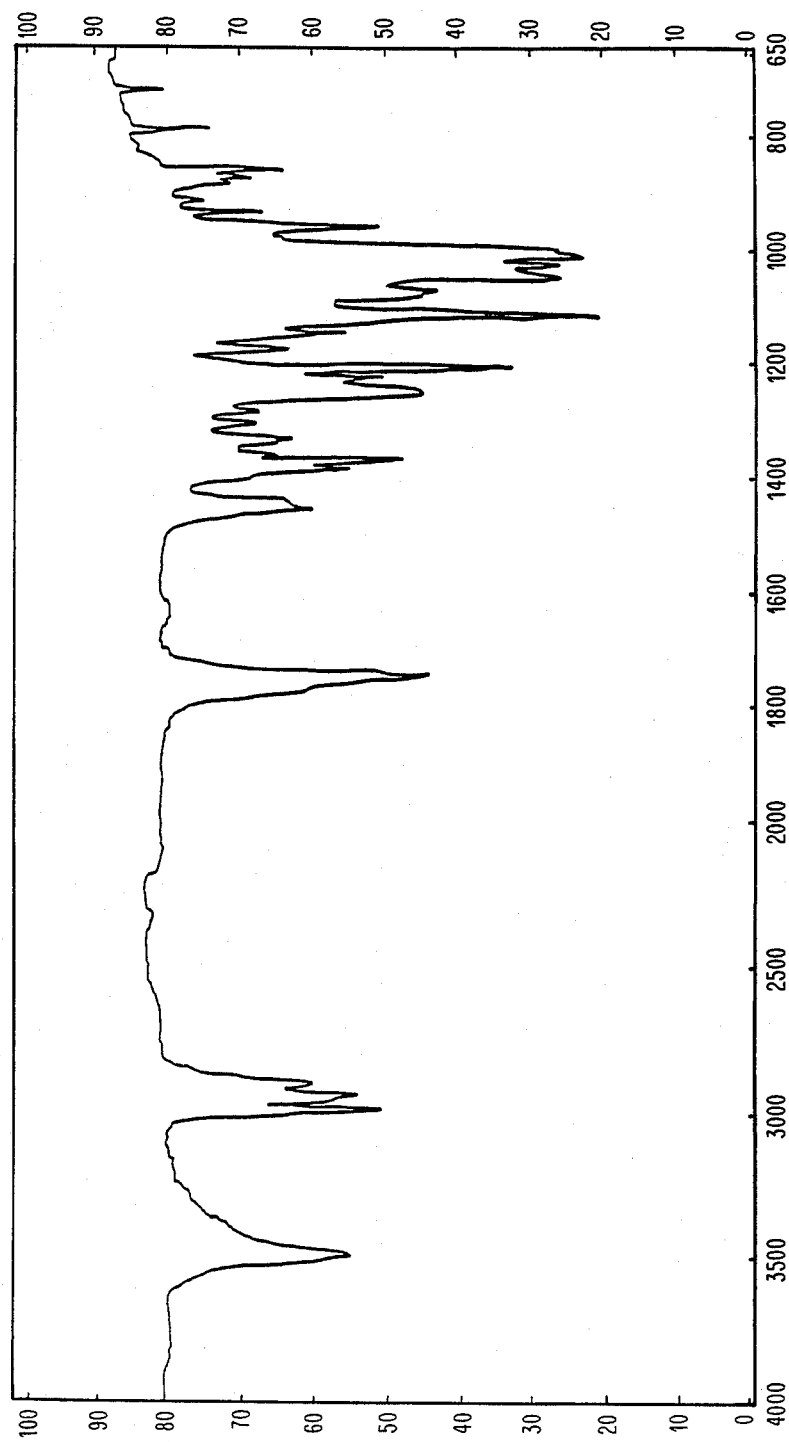
FIG. 4 shows ir spectra of SEN-366-A$_4$ of the present invention. The measuring condition is KBr disc. The ordinate is transmittances (%) and the abscissa is wave numbers (cm$^{-1}$).
Figure 5:
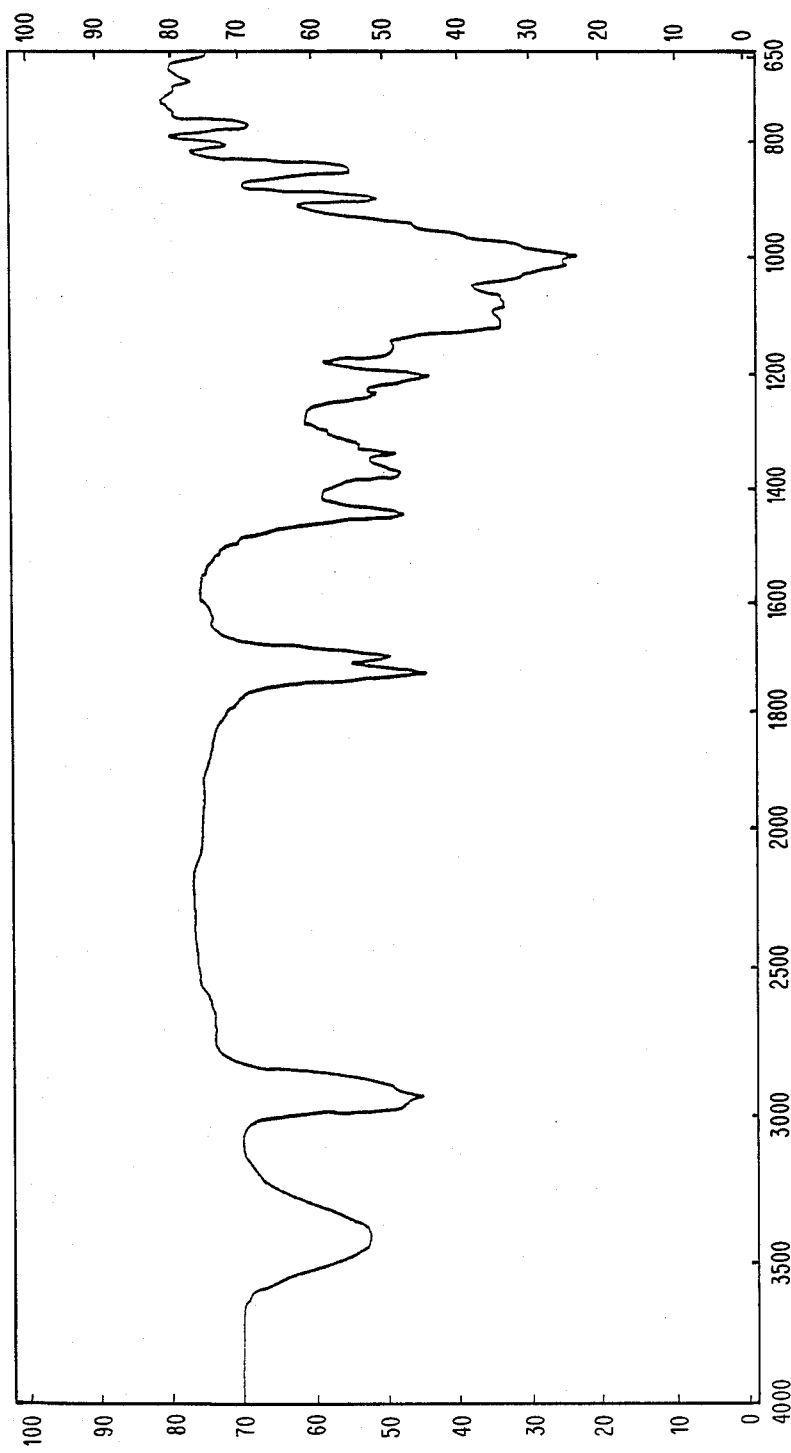
FIG. 5 shows ir spectra of SEN-366-D of the present invention. The measuring condition is KBr disc. The ordinate is transmittances (%) and the abscissa is wave numbers (cm$^{-1}$).
Figure 6:
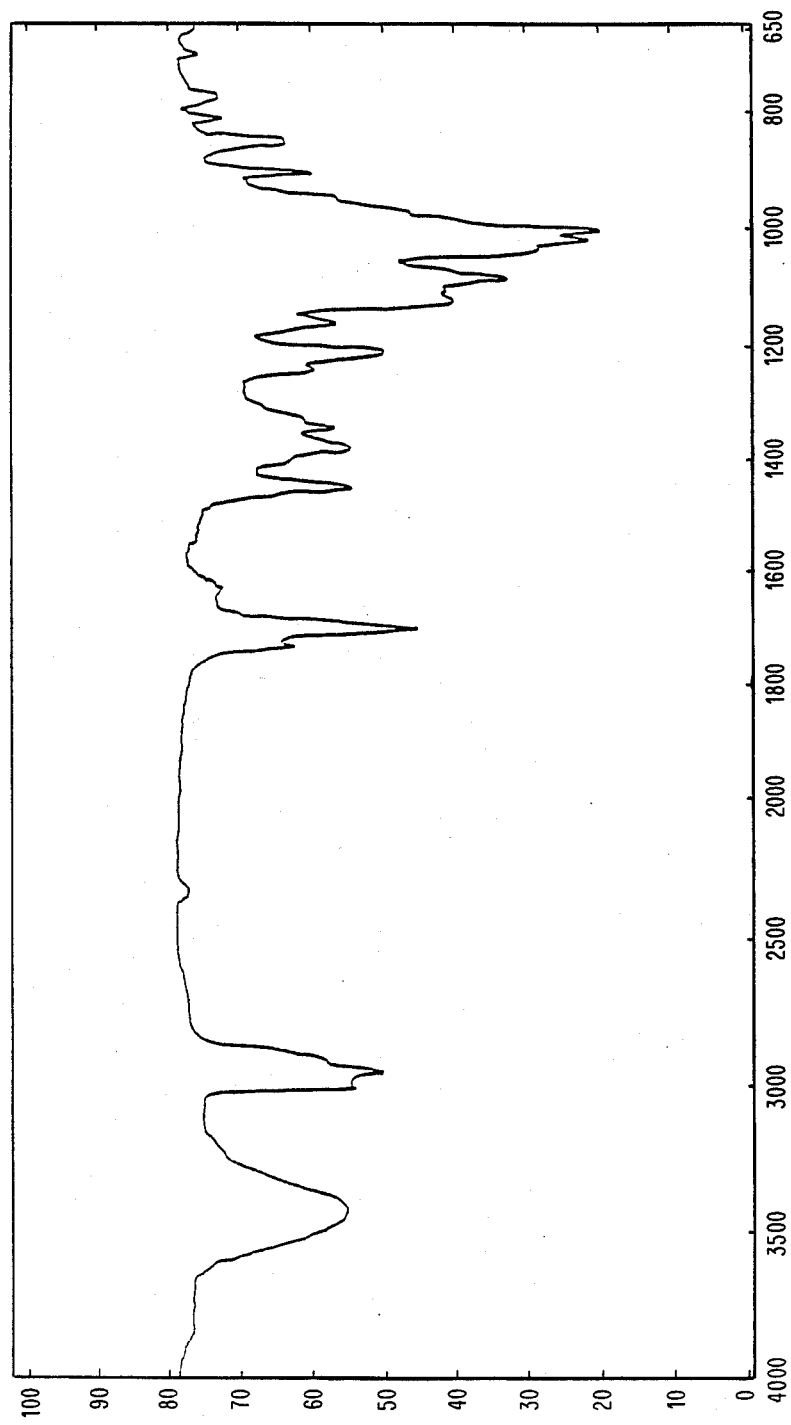
FIG. 6 shows ir spectra of a mixture of SEN-366-D$_1$ and SEN-366-D$_3$ of the present invention. The measuring condition is KBr disc. The ordinate is transmittances (%) and the abscissa is wave numbers (cm$^{-1}$).
Figure 7:
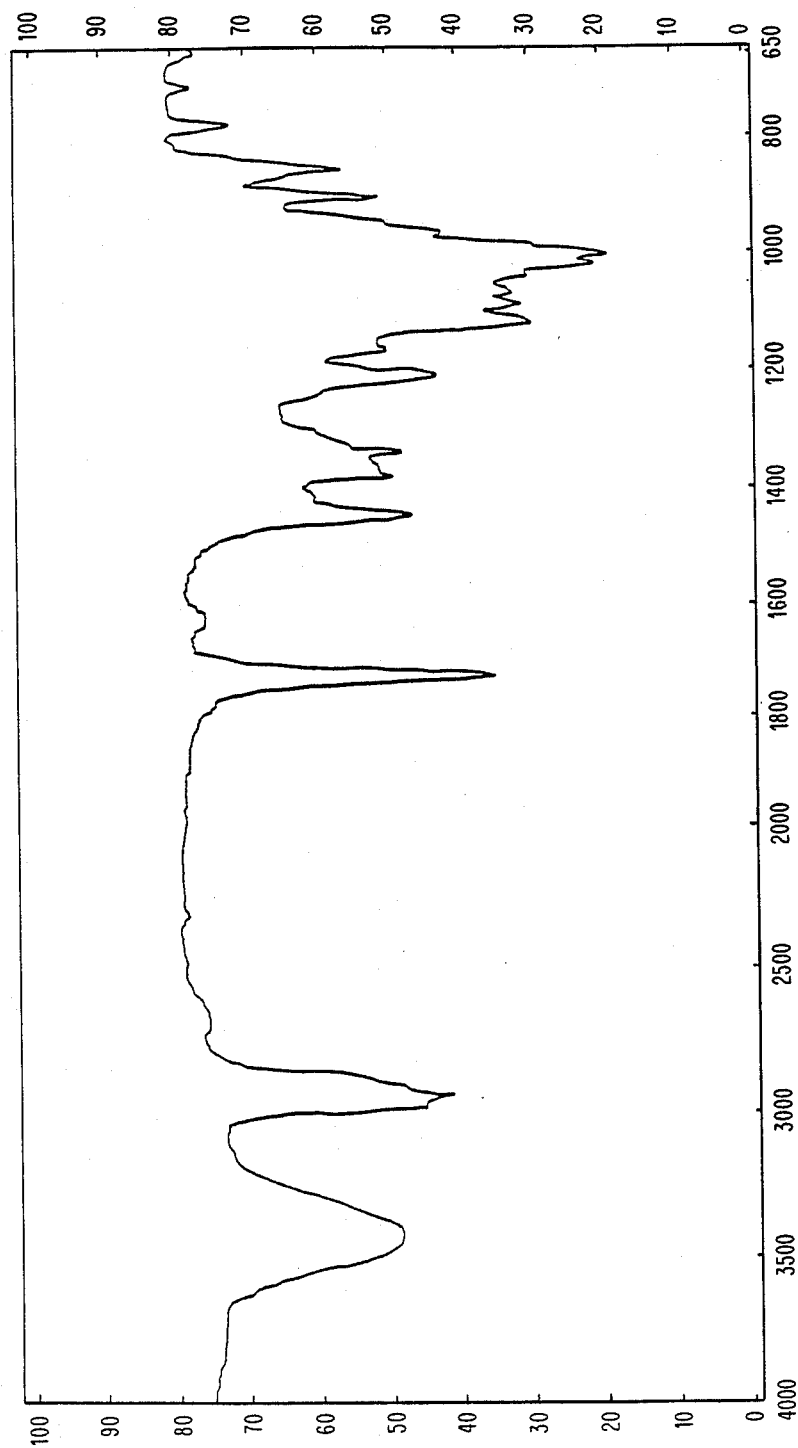
FIG. 7 shows ir spectra of a mixture of SEN-366-D$_2$ and SEN-366-D$_4$ of the present invention. The measuring condition is KBr disc. The ordinate is transmittances (%) and the abscissa is wave numbers (cm$^{-1}$).
Figure 8:
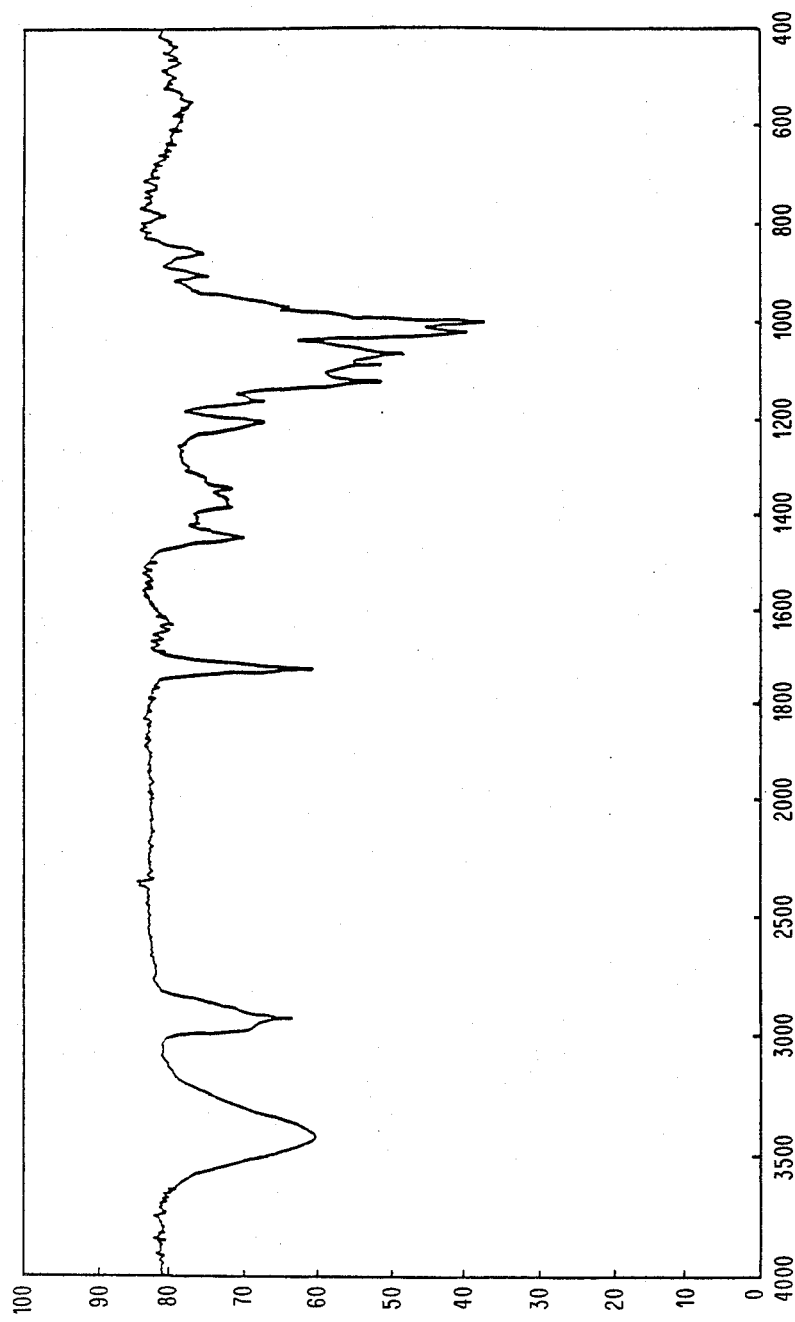
FIG. 8 shows ir spectra of SEN-366-P of the present invention. The measuring condition is KBr disc. The ordinate is transmittances (%) and the abscissa is wave numbers (cm$^{-1}$).
Figure 9:
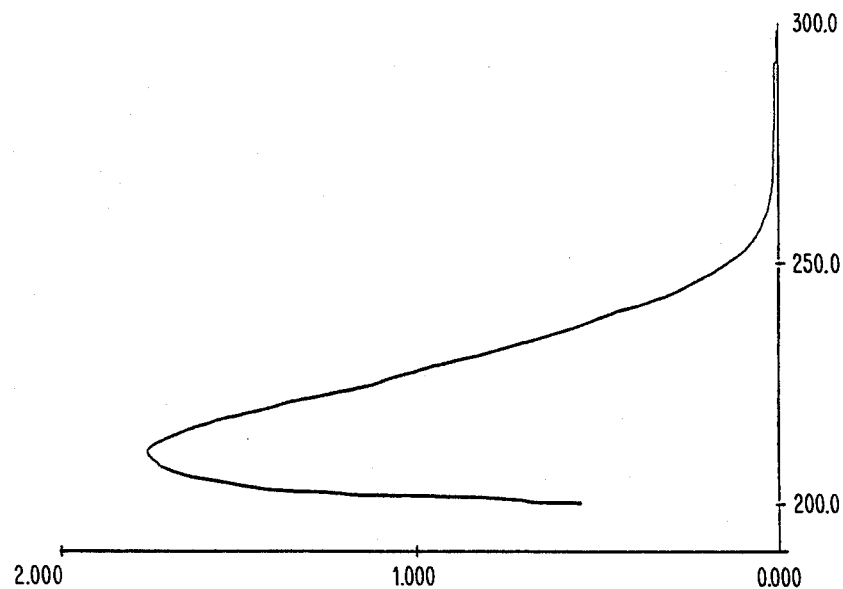
FIG. 9 shows uv spectra of a mixture of SEN-366-D$_1$ and SEN-366-D$_3$ of the present invention. The measuring condition is 0.1% concentration in MeOH. The ordinate is absorbancy and the abscissa is wavelength (nm).
Figure 10:
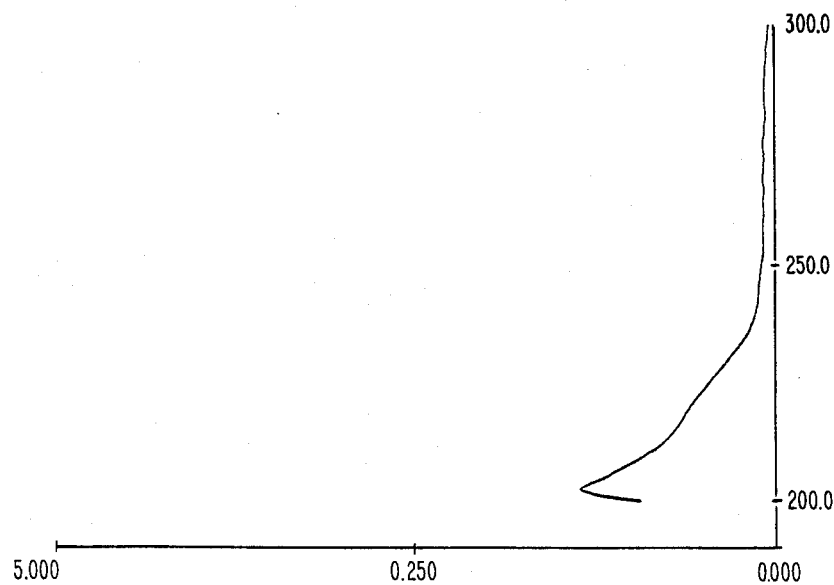
FIG. 10 shows uv spectra of a mixture of SEN-366-D$_2$ and SEN-366-D$_4$ of the present invention. The measuring condition is 0.1% concentration in MeOH. The ordinate is absorbancy and the abscissa is wavelength (nm).
Figure 11:
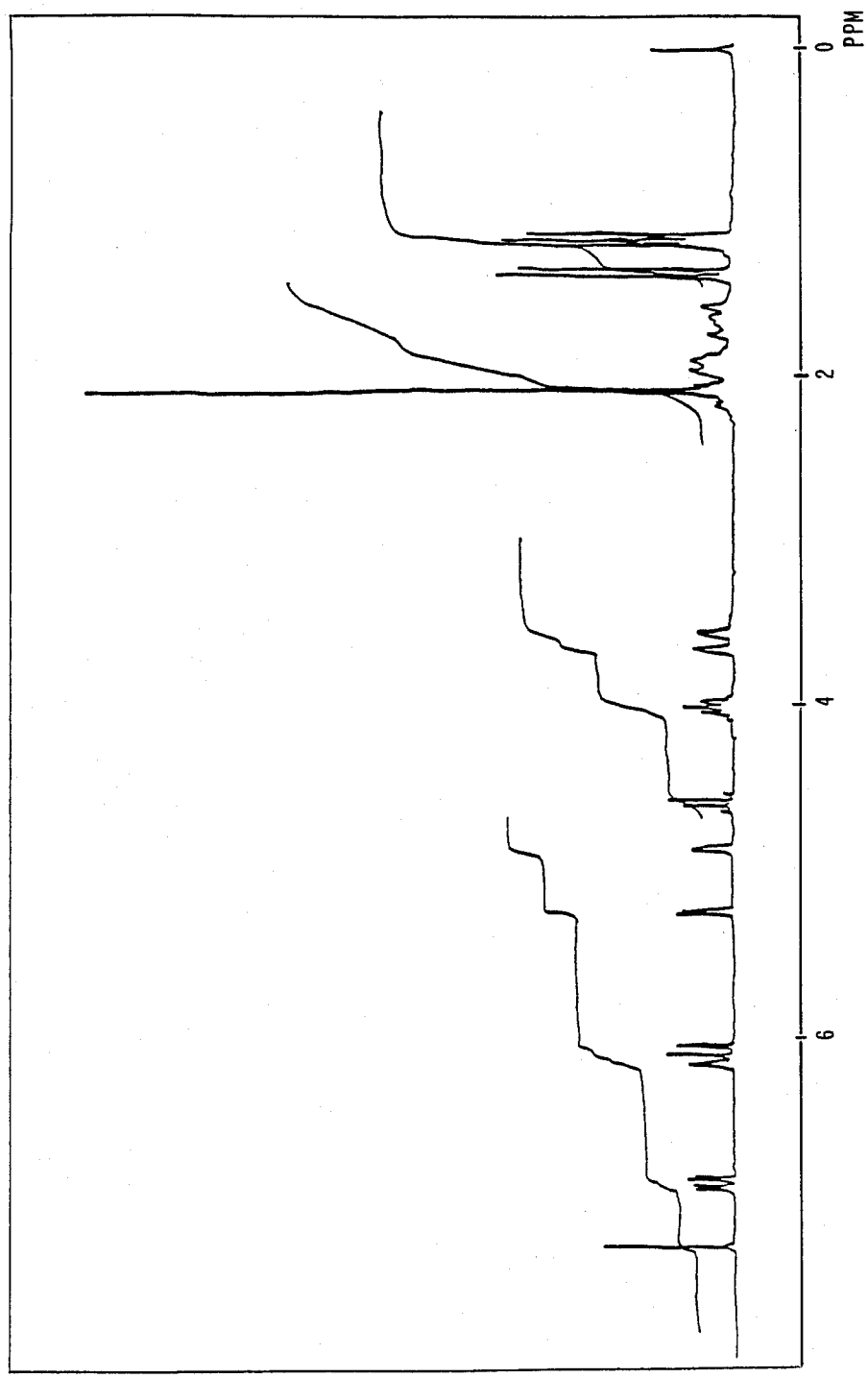
FIG. 11 shows $^1$H nmr spectra of SEN-366-A$_1$ of the present invention. The measuring condition is 200 MHz, in CDCl$_3$, and the internal standard is TMS.
Figure 12:
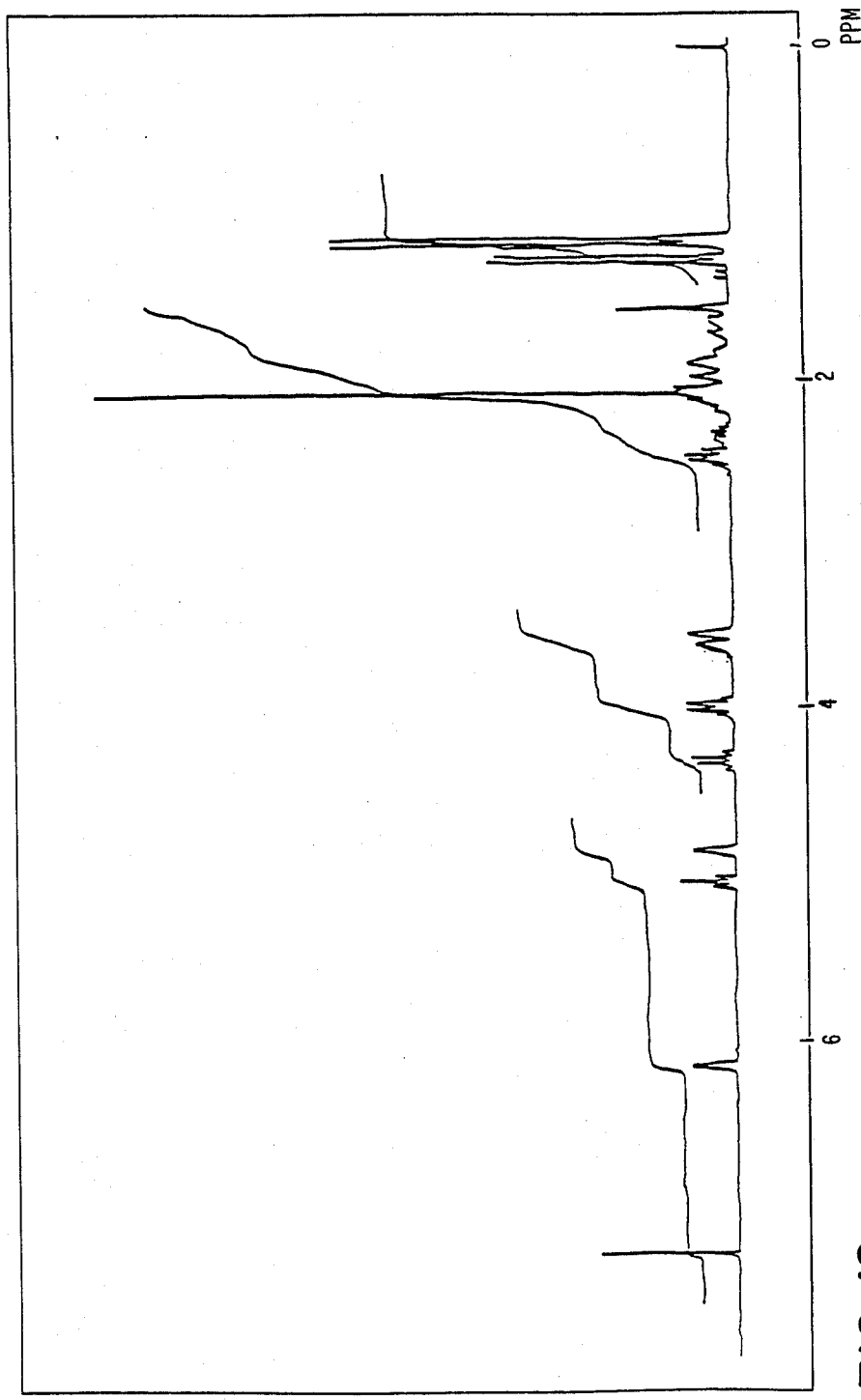
FIG. 12 shows $^1$H nmr spectra of SEN-366-A$_2$ of the present invention. The measuring condition is 200 MHz, in CDCl$_3$ and the internal standard is TMS.
Figure 13:
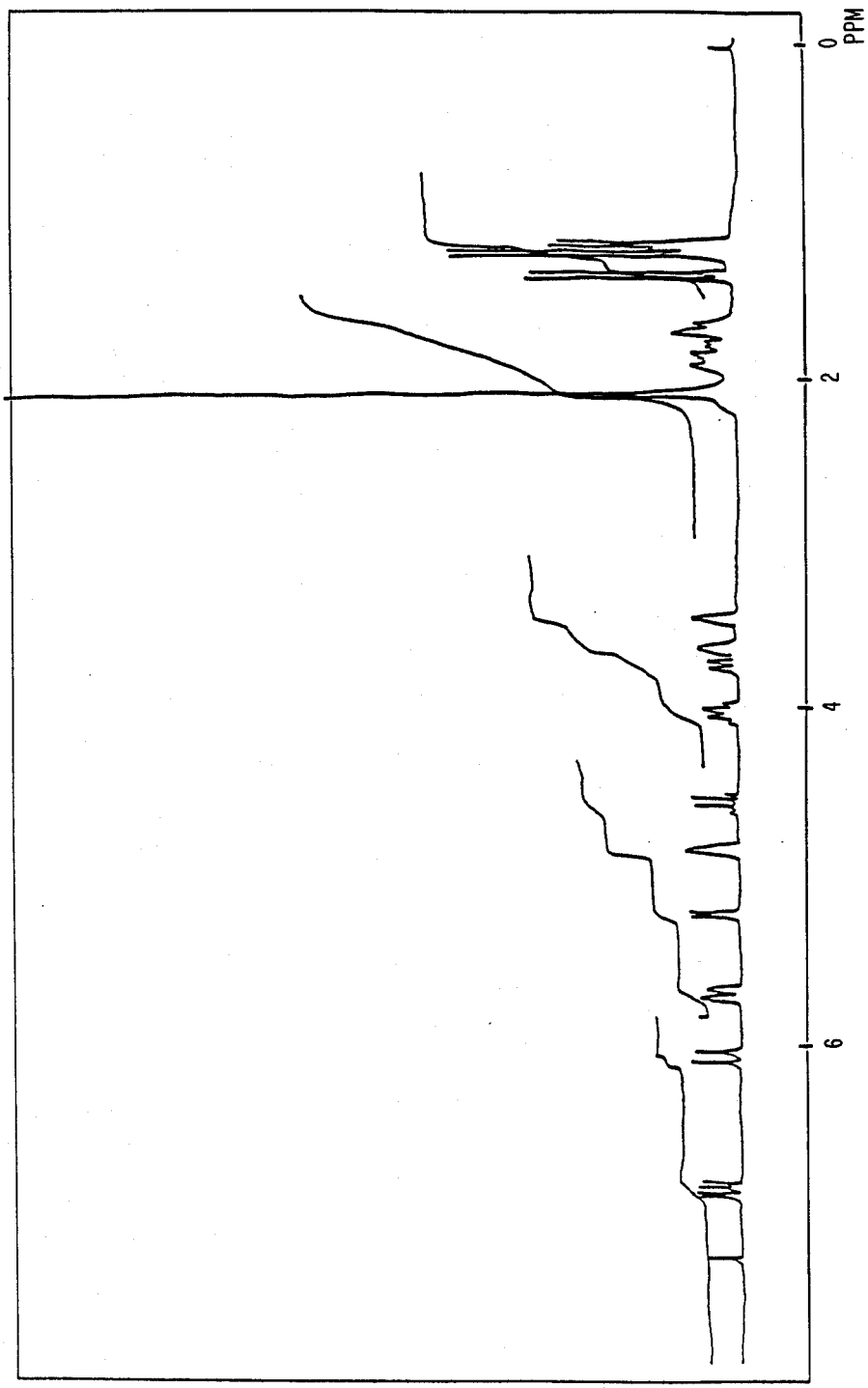
FIG. 13 shows $^1$H nmr spectra of SEN-366-A$_3$ of the present invention. The measuring condition is 200 MHz, in CDCl$_3$ and the internal standard is TMS.
Figure 14:
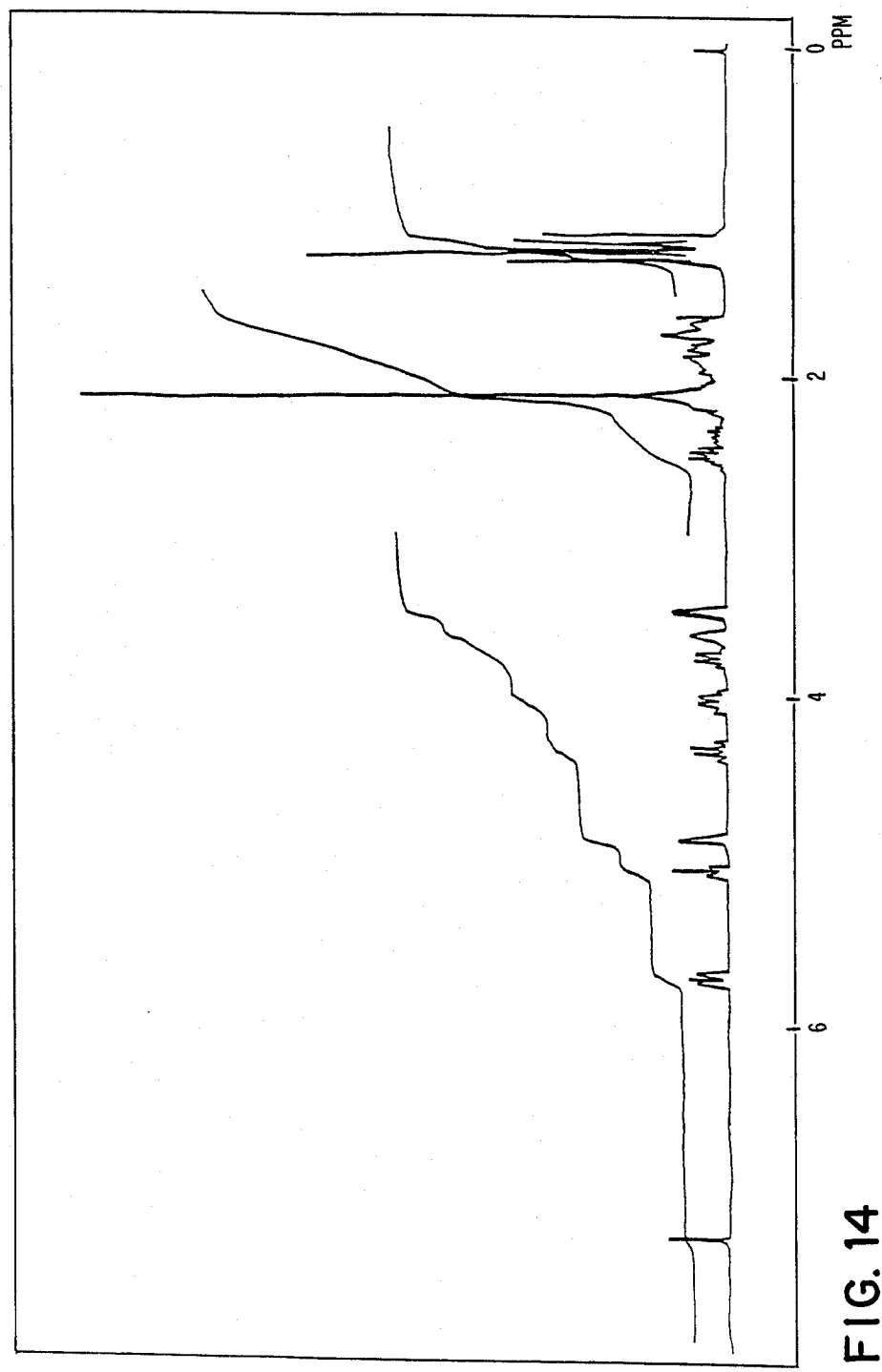
FIG. 14 shows $^1$H nmr spectra of SEN-366-A$_4$ of the present invention. The measuring condition is 200 MHz, in CDCl$_3$ and the internal standard is TMS.
Figure 15:
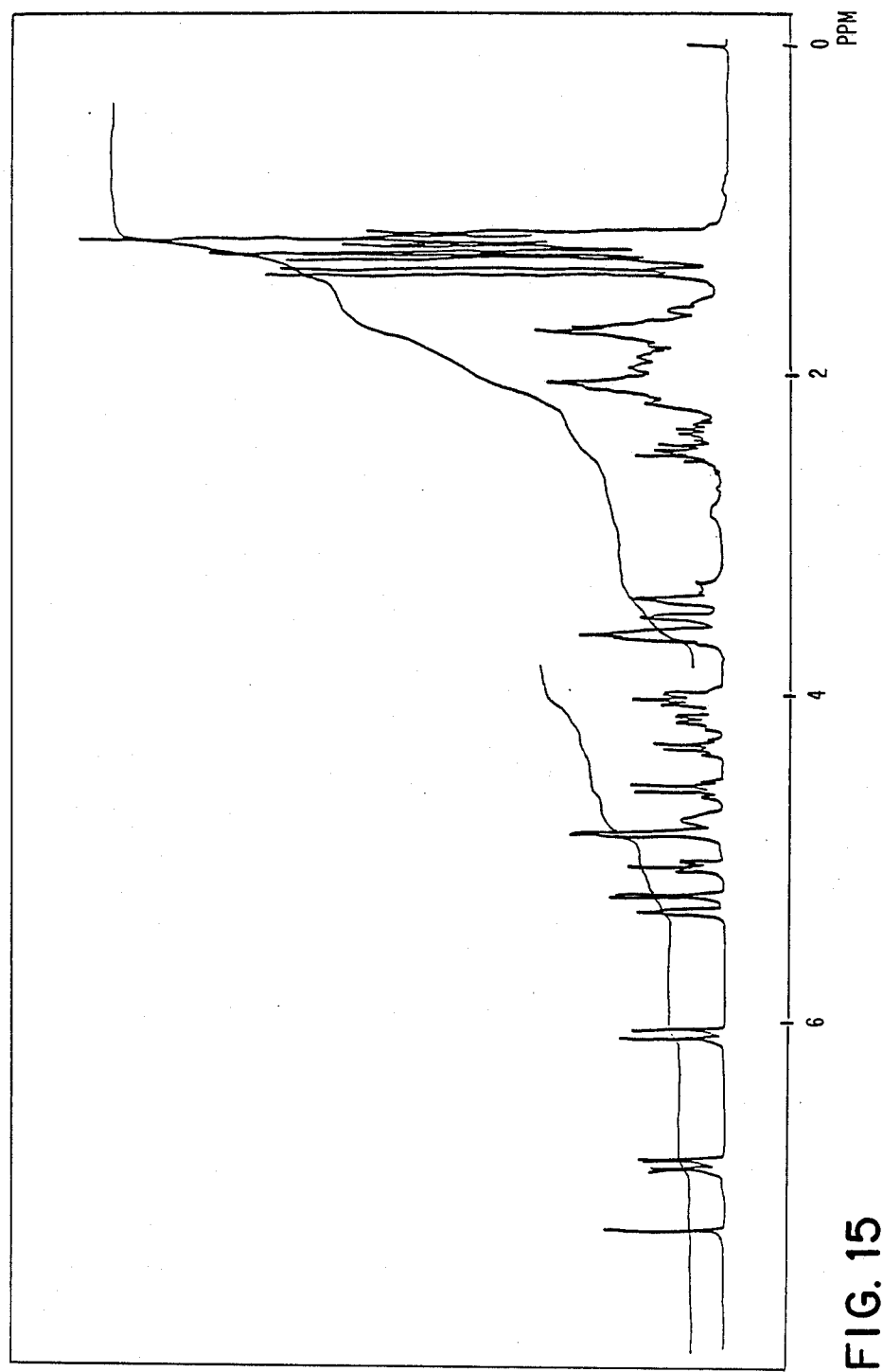
FIG. 15 shows $^1$H nmr spectra of SEN-366-D of the present invention. The measuring condition is 200 MHz, in CDCl$_3$, and the internal standard is TMS.
Figure 16:
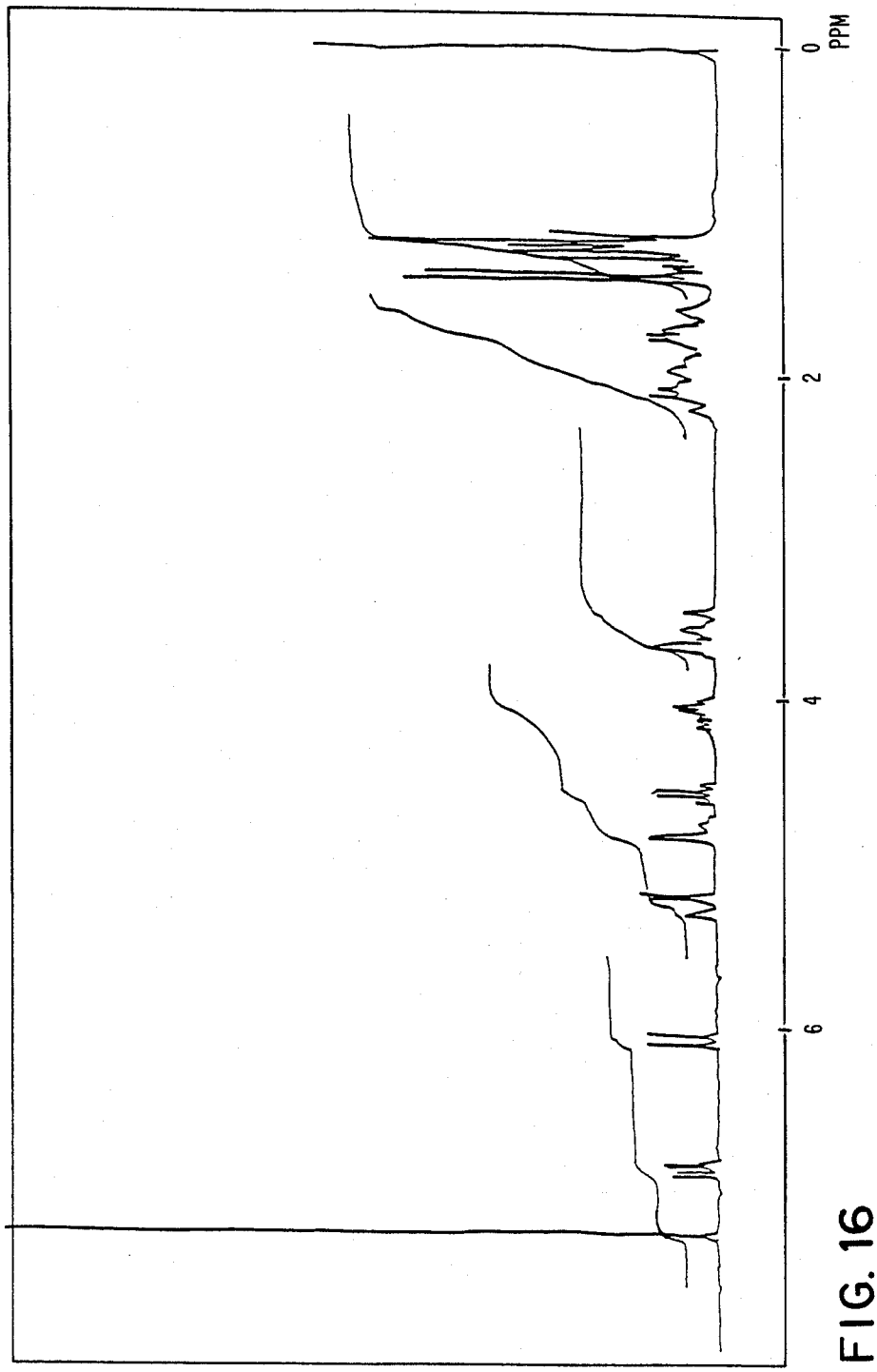
FIG. 16 shows $^1$H nmr spectra of SEN-366-D$_1$/SEN-366-D$_3$ mixture of the present invention. The measuring condition is 200 MHz, in CDCl$_3$ and the internal standard is TMS.
Figure 17:
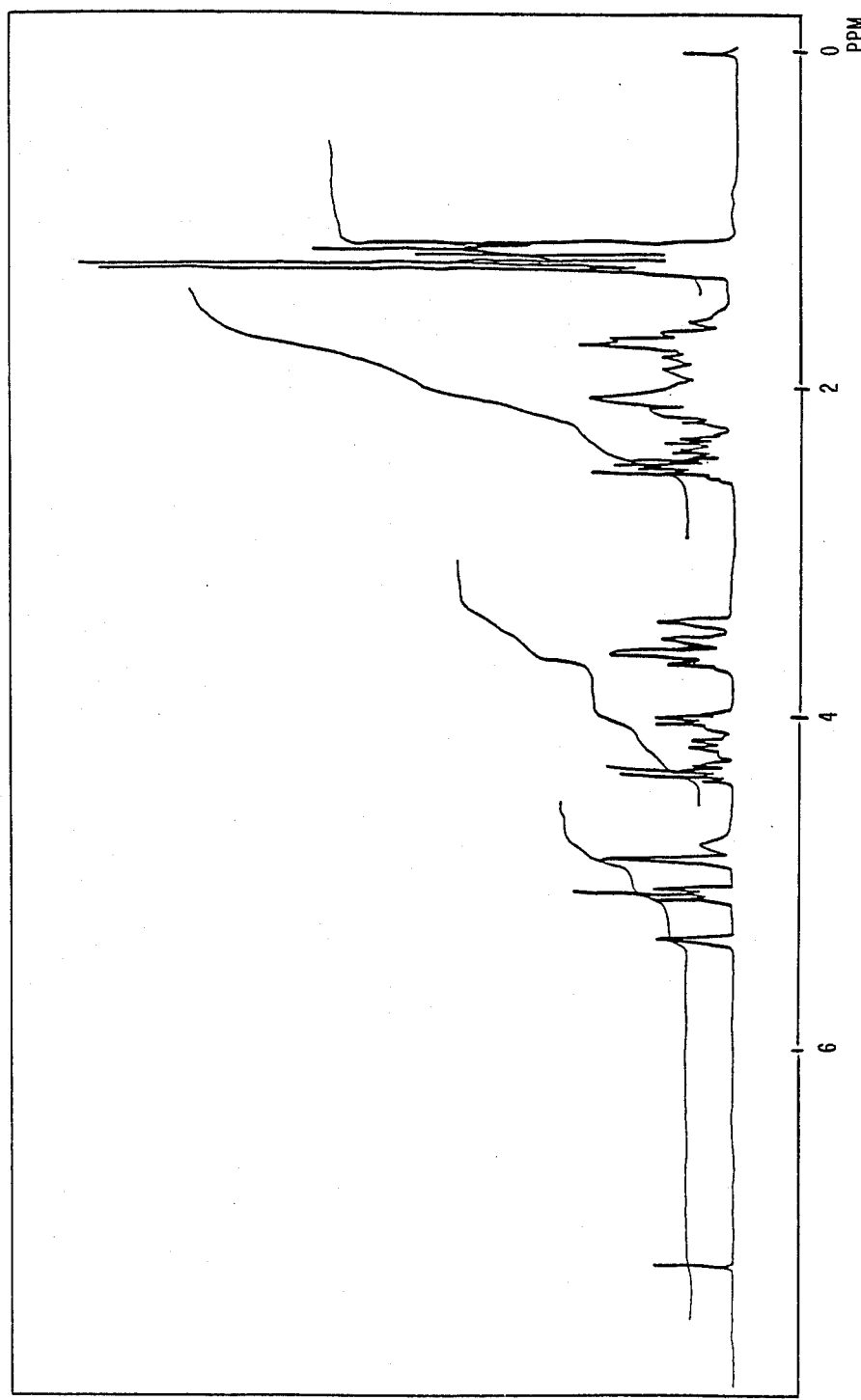
FIG. 17 is $^1$H nmr spectra of SEN-366-D$_2$/SEN-366-D$_4$ mixture of the present invention. The measuring condition is 200 MHz, in CDCl$_3$ and the internal standard is TMS.
Figure 18:
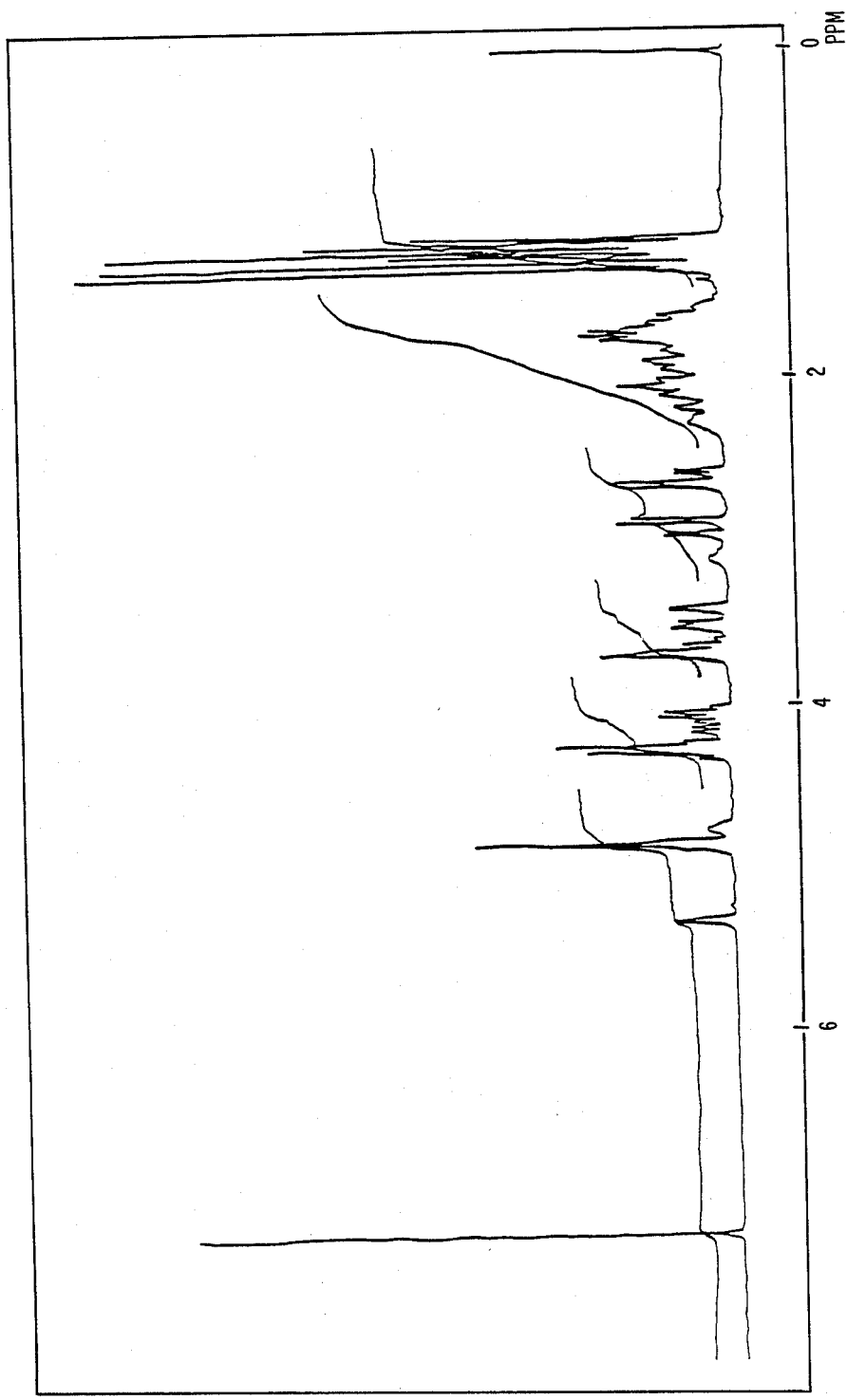
FIG. 18 is $^1$H nmr spectra of SEN-366-P of the present invention. The measuring condition is 200 MHz, in CDCl$_3$ and the internal standard is TMS.
Figure 19:
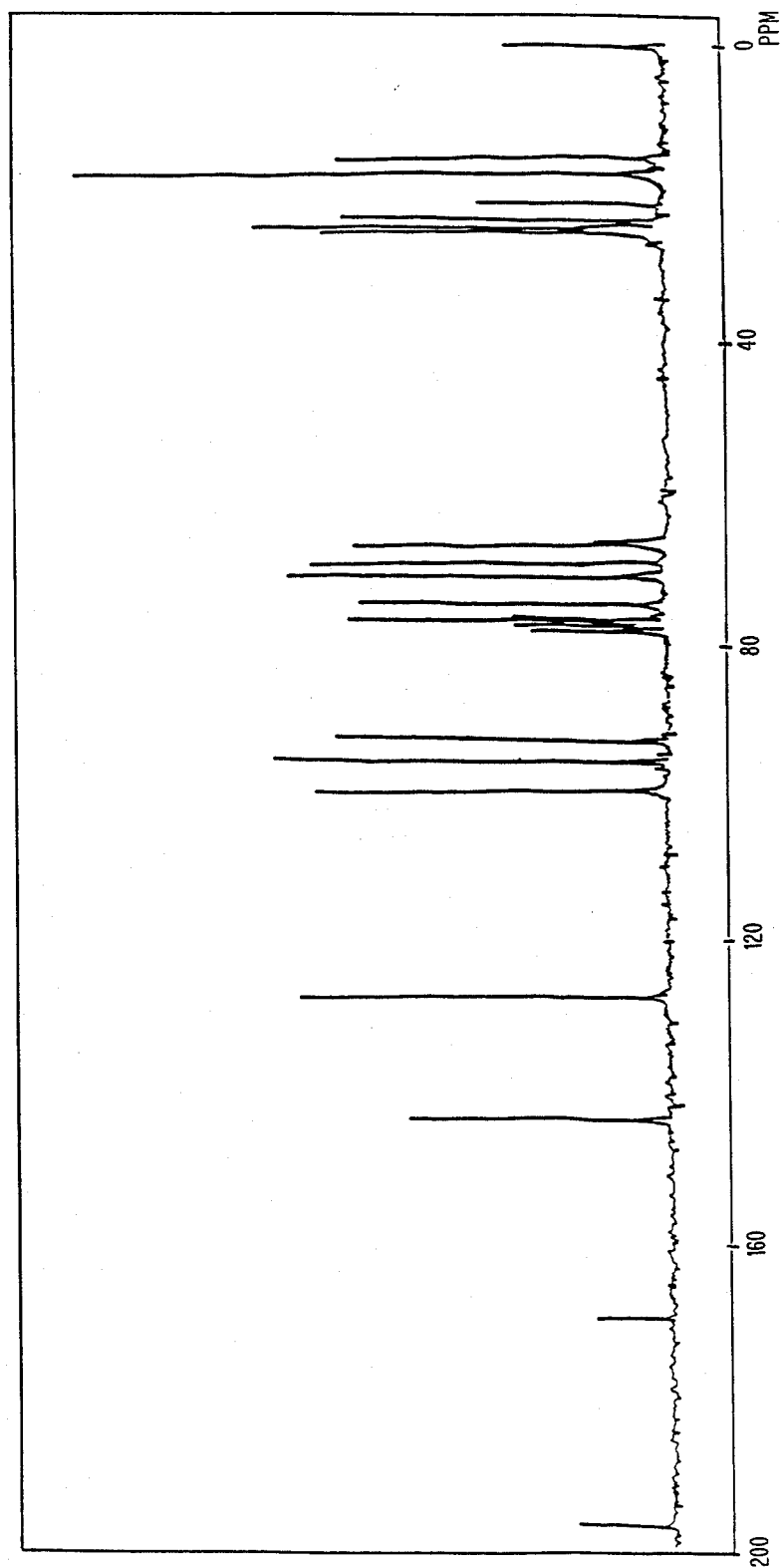
FIG. 19 is $^{13}$C nmr spectra of SEN-366-A$_1$ of the present invention. The measuring condition is 50.3 MHz, in CDCl$_3$ and the internal standard is TMS.
Figure 20:
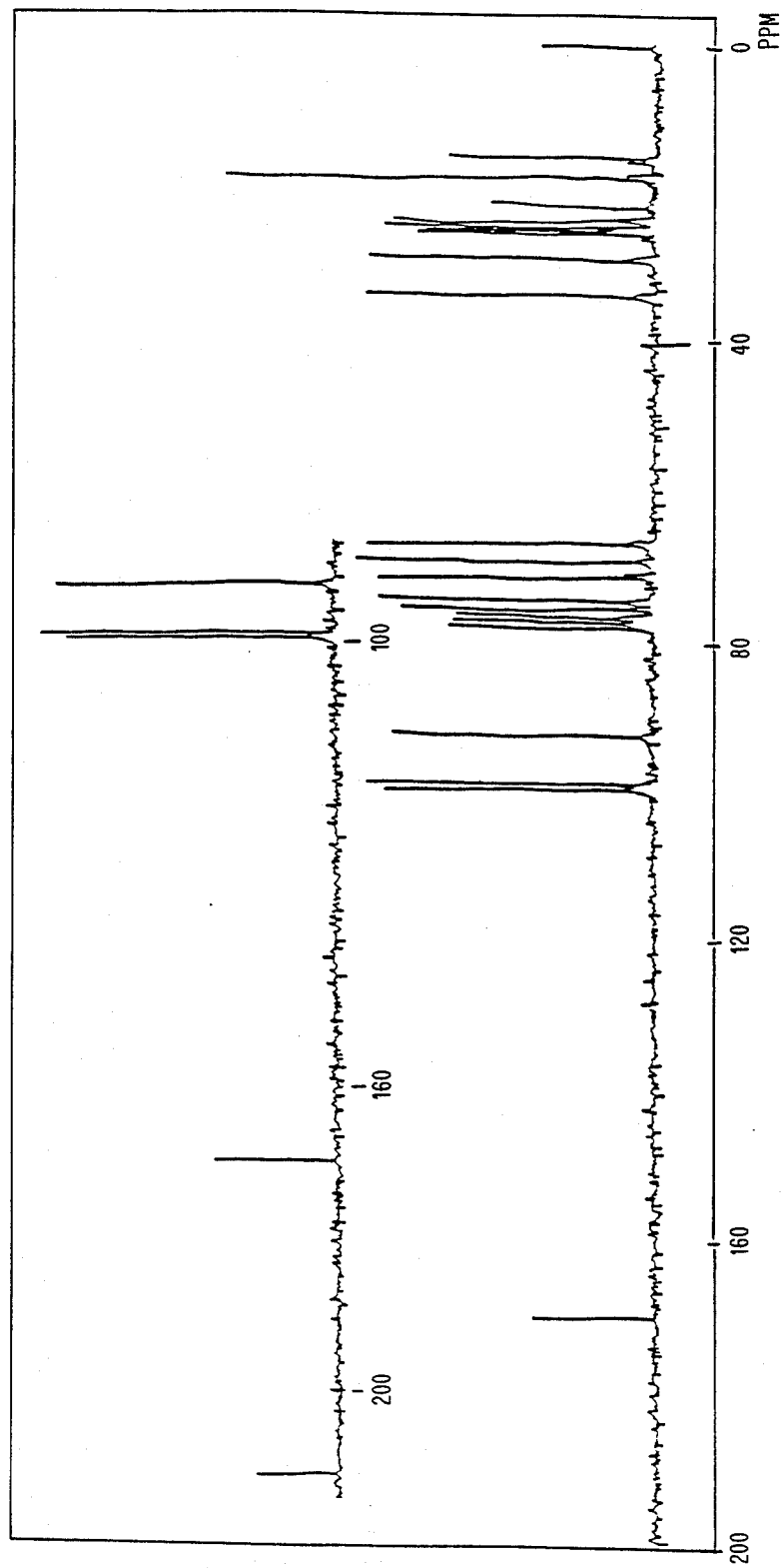
FIG. 20 is $^{13}$C nmr spectra of SEN-366-A$_2$ of the present invention. The measuring condition is 50.3 MHz, in CDCl$_3$ and the internal standard is TMS.
Figure 21:
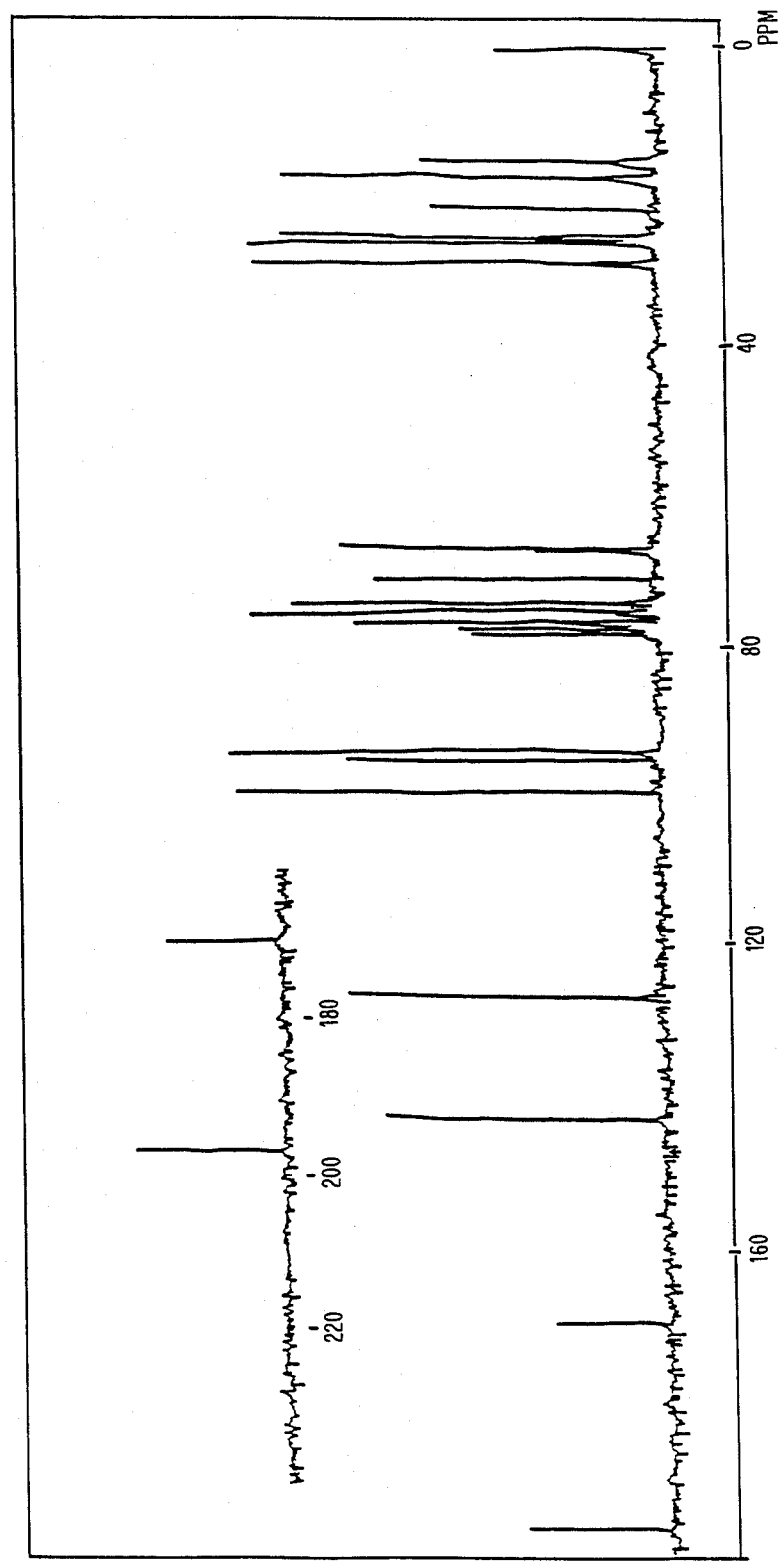
FIG. 21 is $^{13}$C nmr spectra of SEN-366-A$_3$ of the present invention. The measuring condition is 50.3 MHz, in CDCl$_3$ and the internal standard is TMS.
Figure 22:
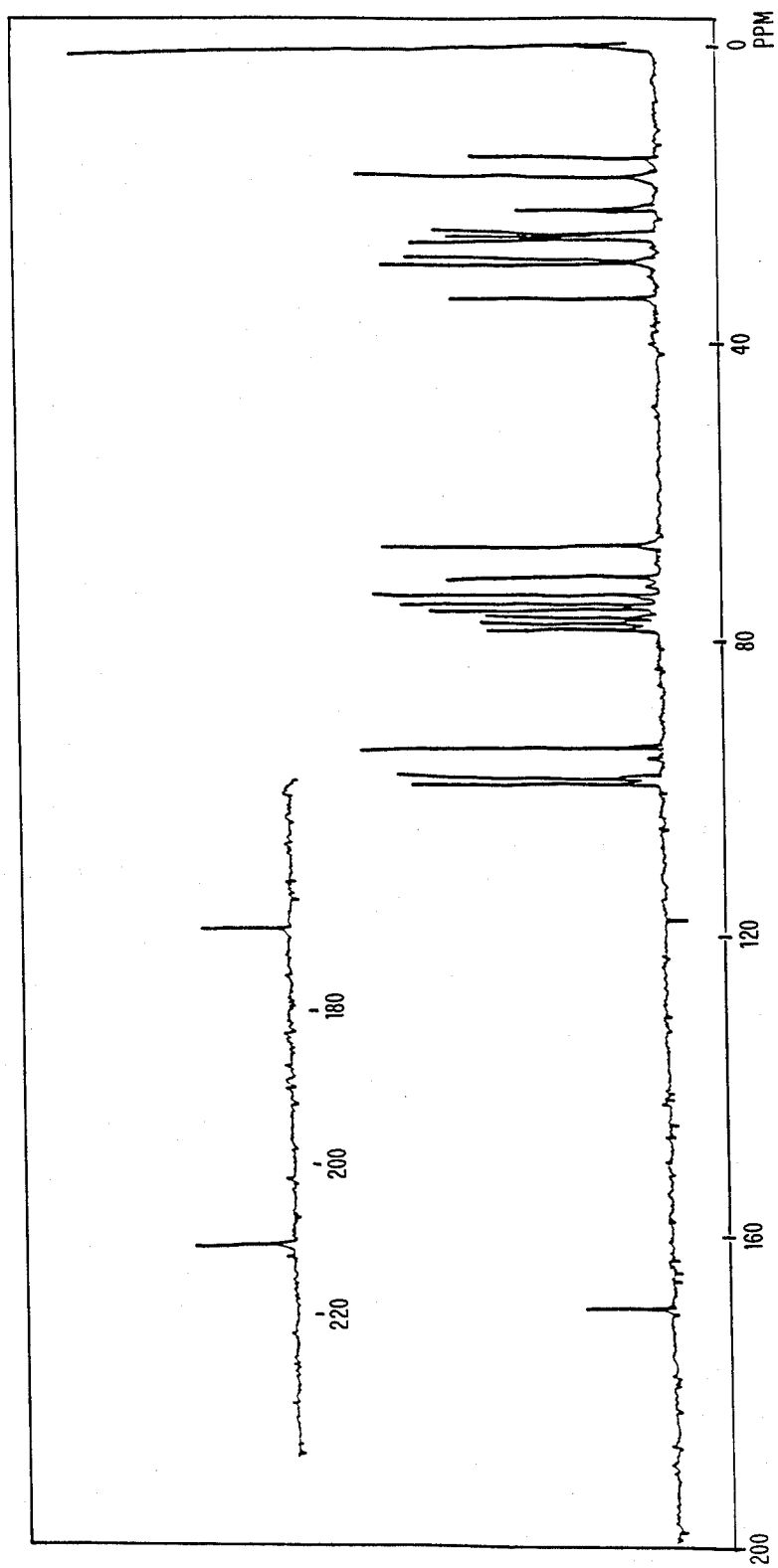
FIG. 22 is $^{13}$C nmr spectra of SEN-366-A$_4$ of the present invention. The measuring condition is 50.3 MHz, in CDCl$_3$ and the internal standard is TMS.
Figure 23:
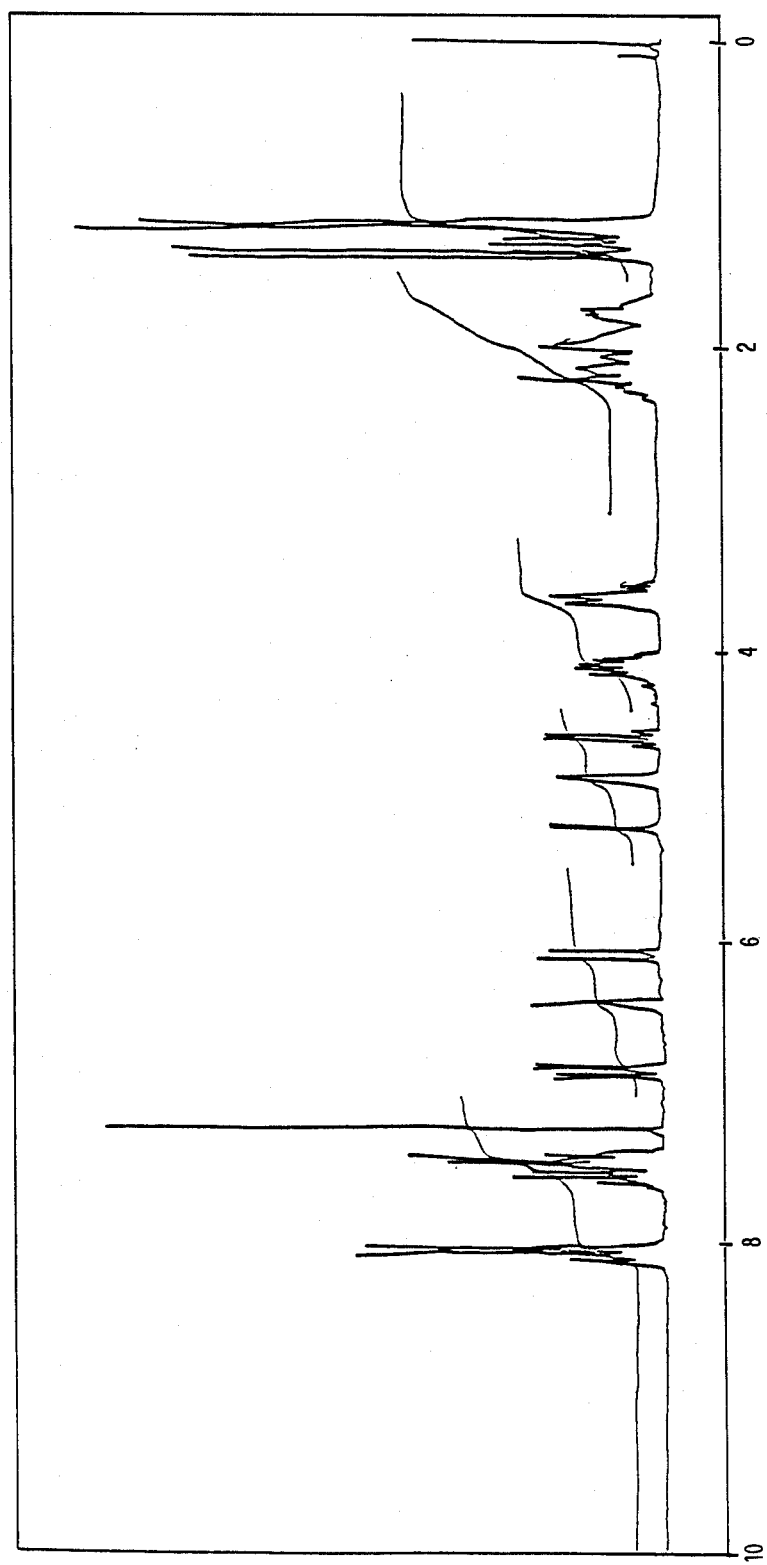
FIG. 23 is $^1$H nmr spectra of SEN-366-B$_1$ of the present invention. The measuring condition is 200 MHz, in CDCl$_2$ and the internal standard is TMS.
Figure 24:
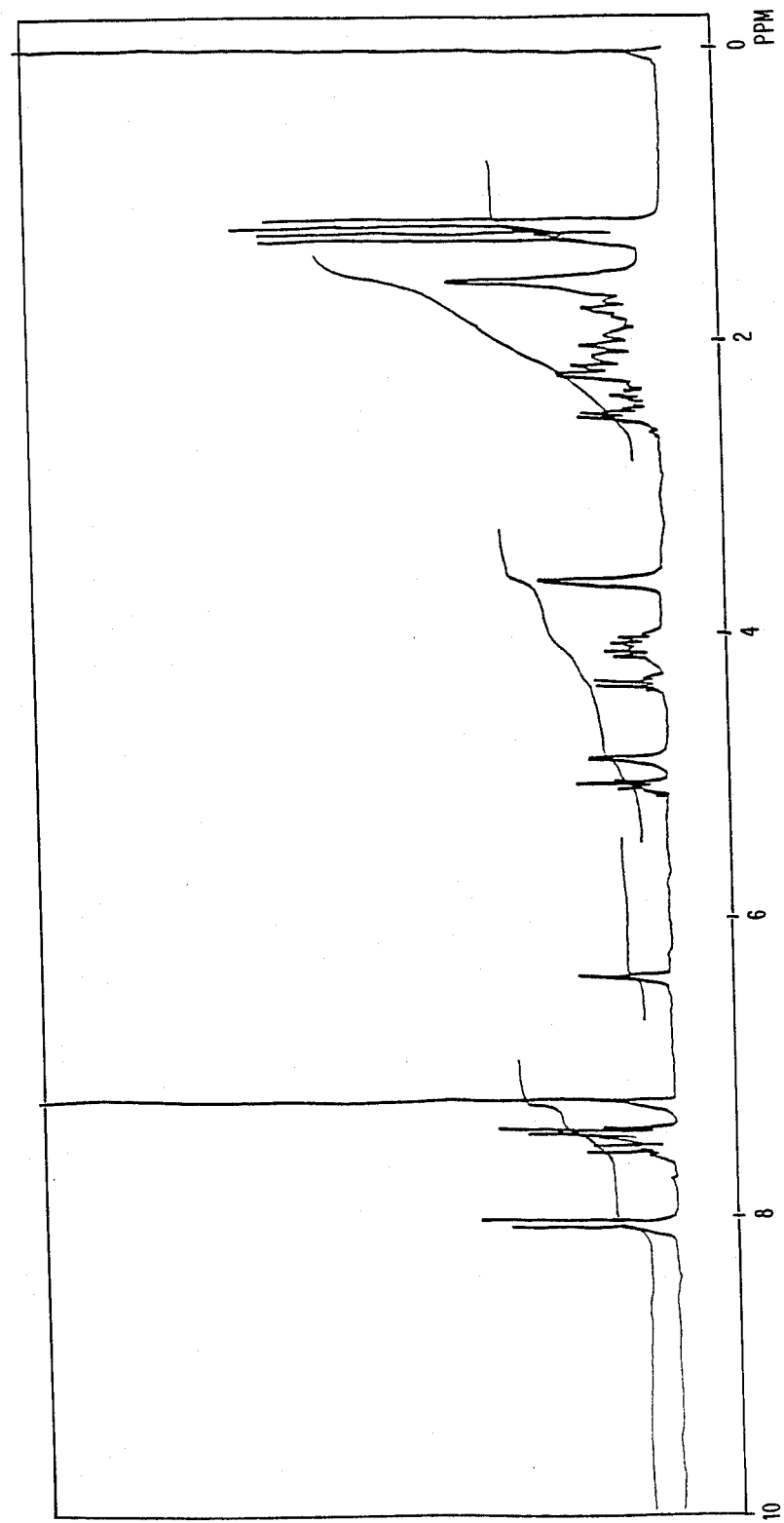
FIG. 24 is $^1$H nmr spectra of SEN-366-B$_2$ of the present invention. The measuring condition is 200 MHz, in CDCl$_3$ and the internal standard is TMS.
Figure 25:
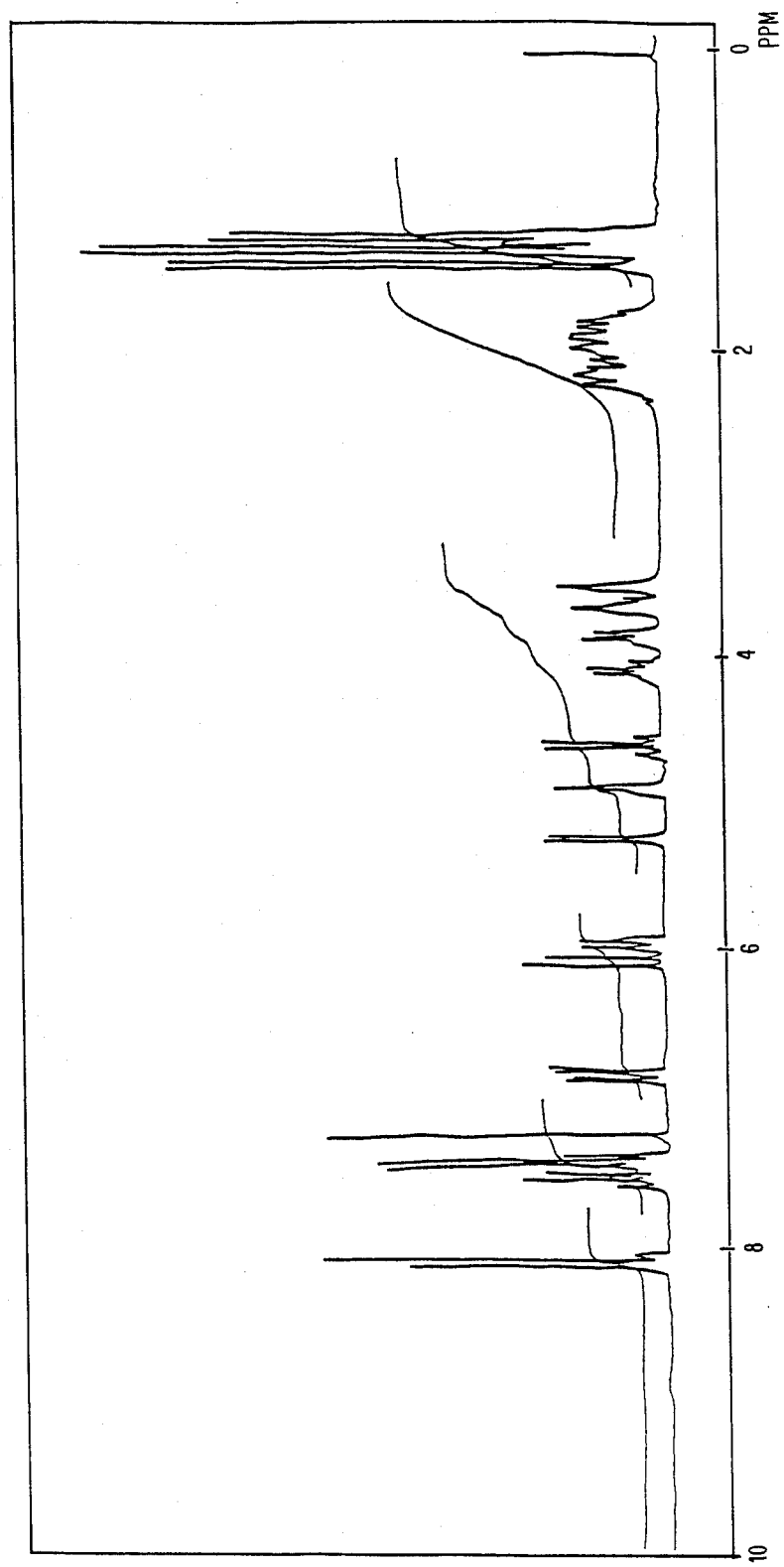
FIG. 25 is $^1$H nmr spectra of SEN-366-B$_3$ of the present invention. The measuring condition is 200 MHz, in CDCl$_3$ and the internal standard is TMS.
Figure 26:
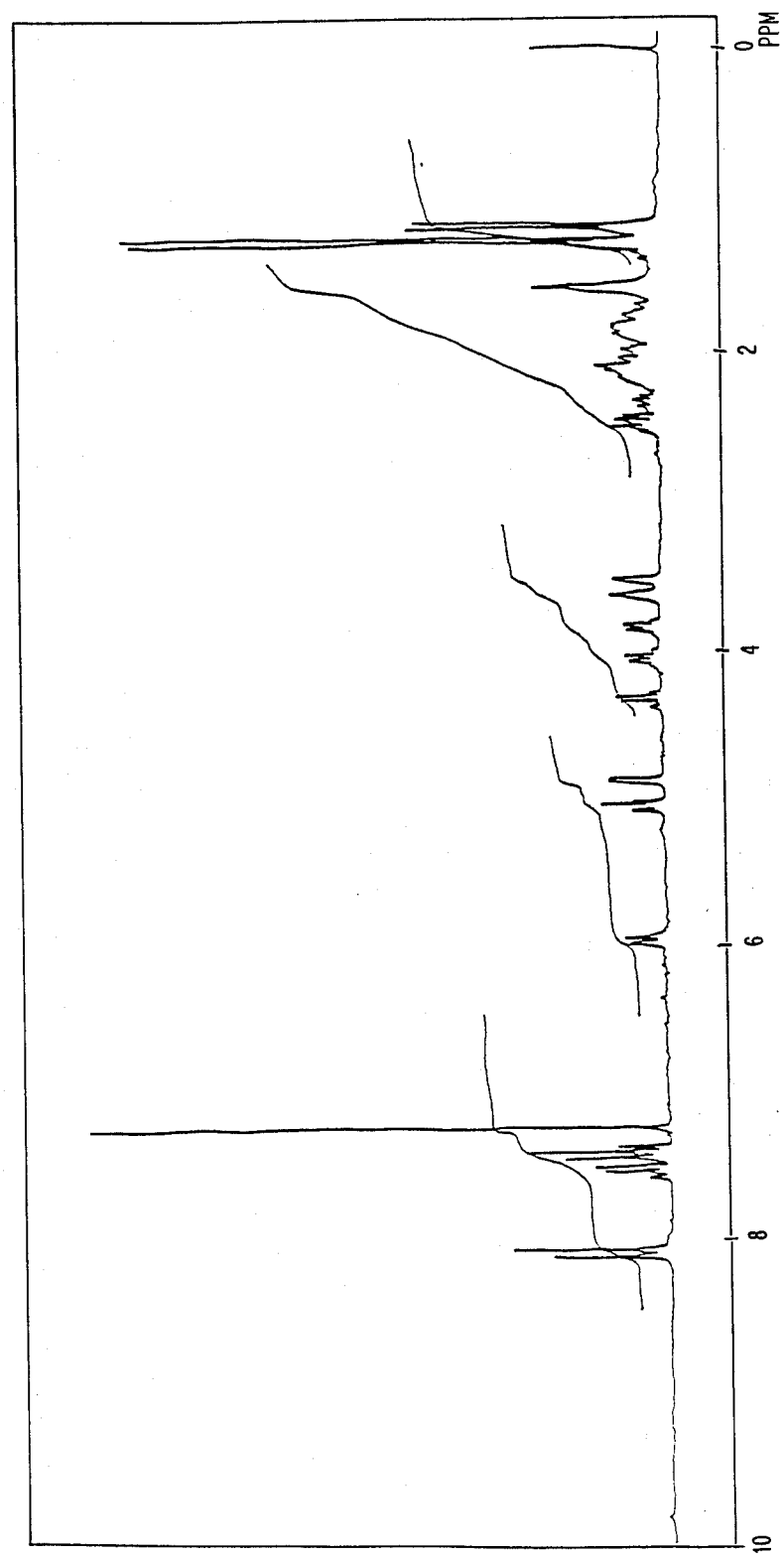
FIG. 26 is $^1$H nmr spectra of SEN-366-B$_4$ of the present invention. The measuring condition is 200 MHz, in CDCl$_3$ and the internal standard is TMS.
Figure 27:
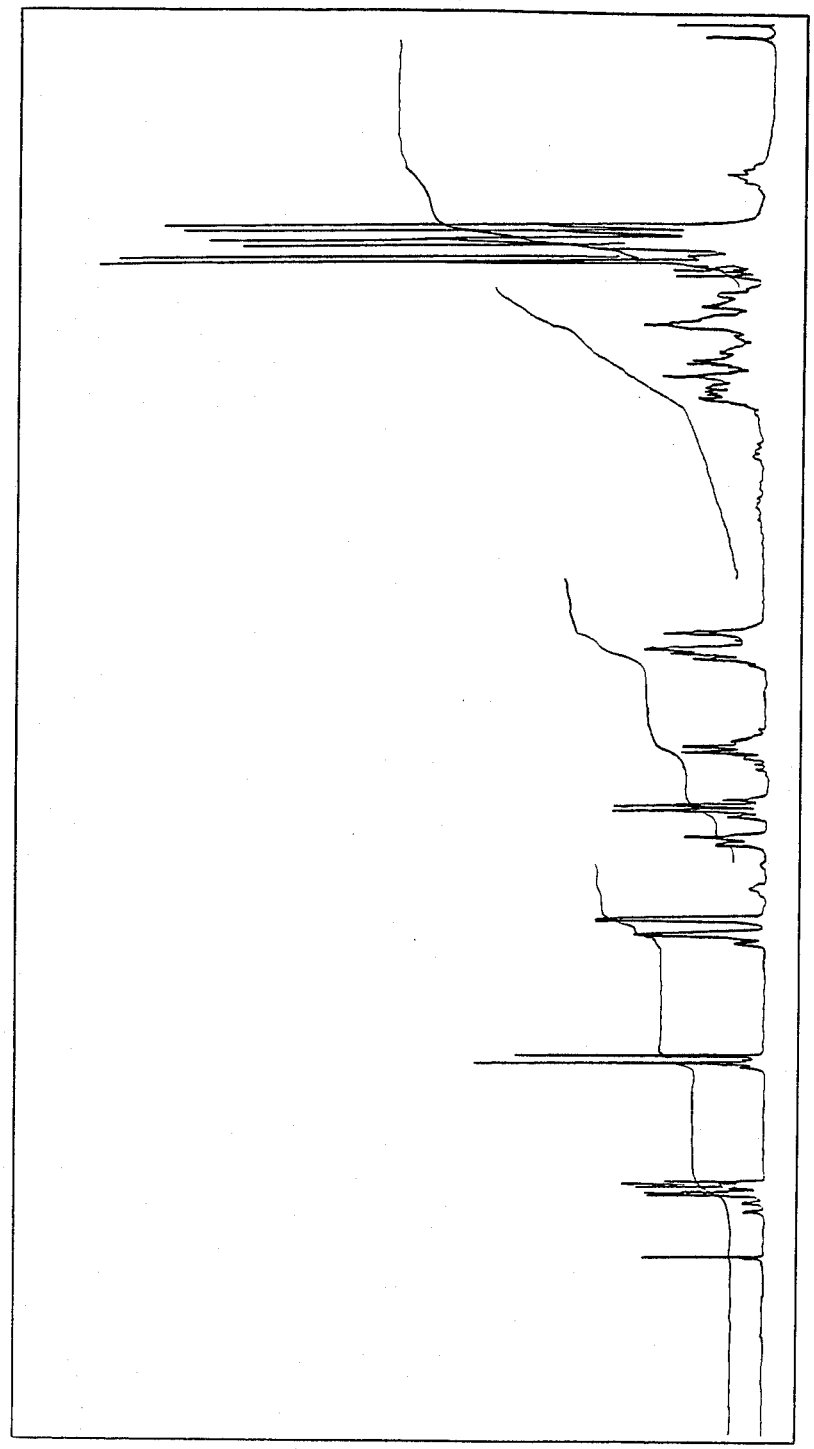
FIG. 27 shows $^1$H nmr spectra of SEN-366-F$_O$ of the present invention. Measuring condition is 200 MHz, in CDCl$_3$ and the internal standard is TMS.
Figure 28:
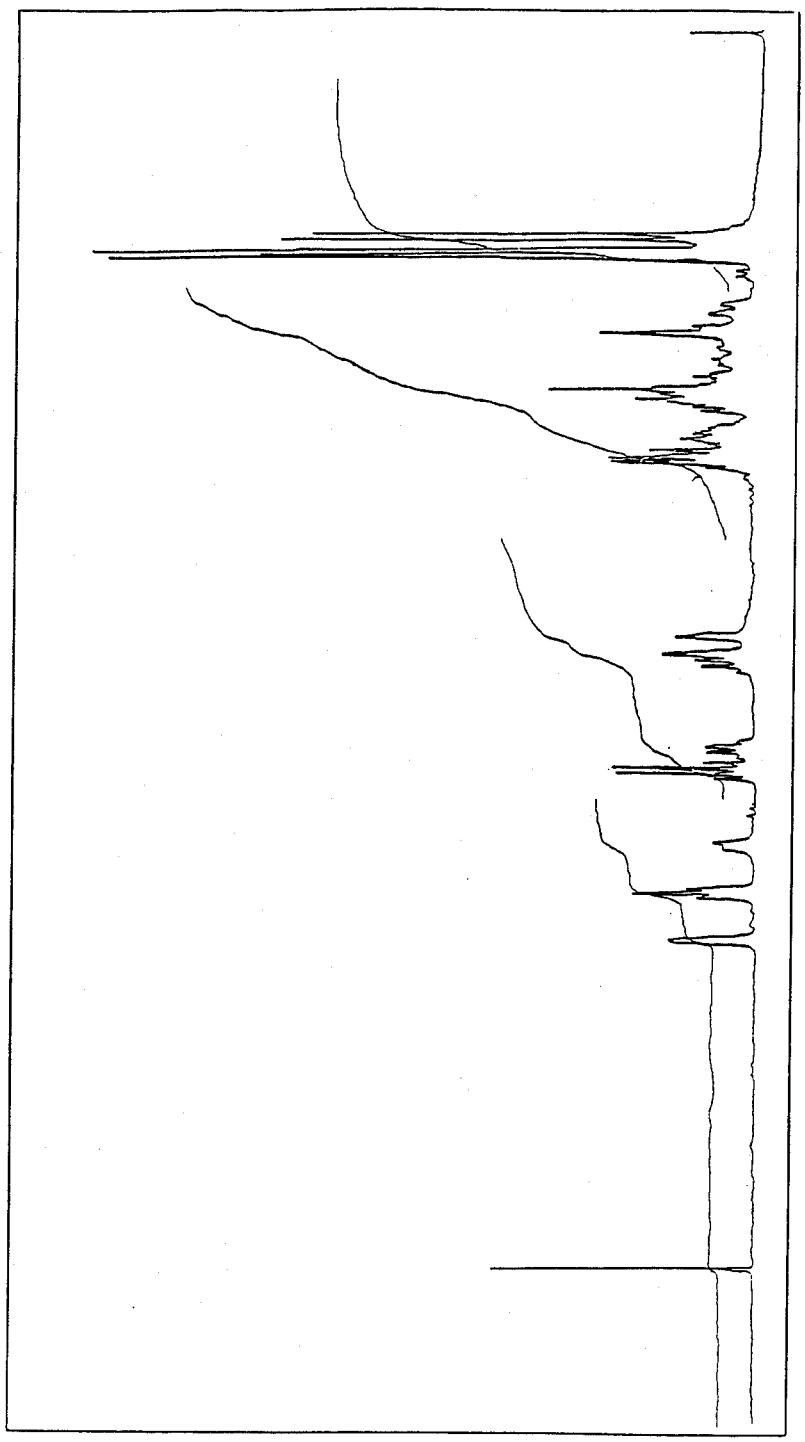
FIG. 28 shows $^1$H nmr spectra of SEN-366-F$_H$ of the present invention. Measuring condition is 200 MHz, in CDCl$_3$ and the internal standard is TMS.

We claim:

1. A compound of the formula (I):

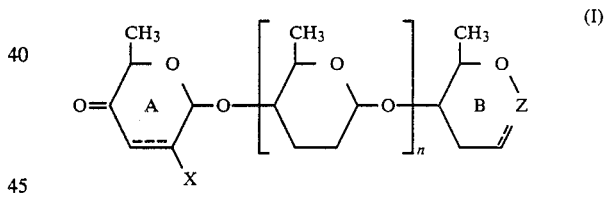

in which:
═ is a single bond or a double bond,
X is hydrogen or hydroxy,
n is 0 or 1,
Z is

when ═ in ring B is a double bond, and, when ═ in ring B is a single bond, Z is

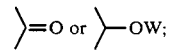

wherein W is hydrogen, lower acyl, unsubstituted benzoyl, lower alkyl or benzoyl substituted by 1 to 5 halogen.

2. A compound of the formula (II):

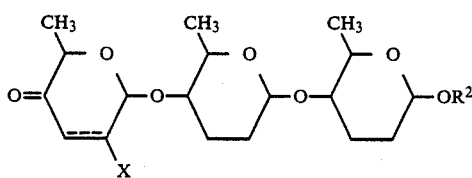 (II)

in which $R^2$ is hydrogen, lower acyl or unsubstituted benzoyl; X is hydrogen or hydroxy; and $\equiv\equiv\equiv$ is a single or double bond.

3. A compound of formula (V):

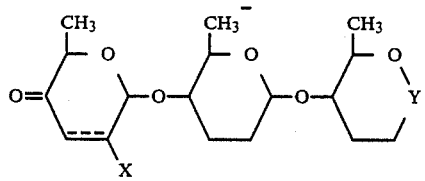 (V)

in which Y is $=C=O$ or $=CHOR^5$, where $R^5$ is $C_{1-4}$ lower alkyl or benzoyl substituted by 1 to 5 halogen; X is hydrogen or hydroxy; and $\equiv\equiv\equiv$ is a single or double bond.

4. A compound of the formula (VIII):

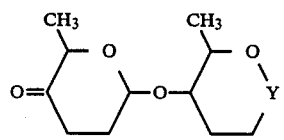 (VIII)

in which Y is $=C=O$ or $=CHOR^8$ or $R^8$ is hydrogen, lower alkyl, lower acyl or benzoyl, unsubstituted or substituted by 1 to 5 halogen and $\equiv\equiv\equiv$ is a single or double bond.

5. A compound of the formula (X):

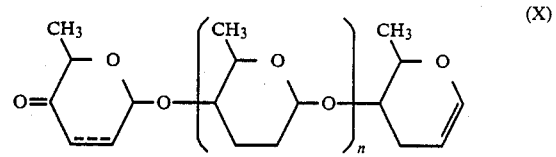 (X)

in which n is 0 or 1; and $\equiv\equiv\equiv$ is a single or double bond.

6. A compound according to claim 1, having the formula (IV):

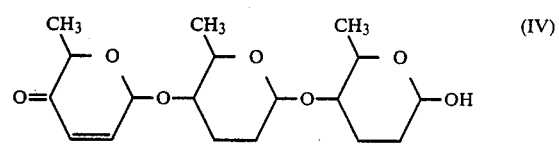 (IV)

7. A pharmaceutical composition useful for inhibiting the aggregation of platelets, which comprises a platelet aggregation inhibiting effective amount of a compound according to claim 1 in combination with a pharmaceutically acceptable diluent or carrier therefor.

8. A method for inhibiting the aggregation of platelets in animals, including humans, which comprises administering to an animal, including humans, in need thereof a platelet aggregation inhibiting effective amount of the compound according to claim 1.

* * * * *